(12) United States Patent
Akama et al.

(10) Patent No.: US 10,725,048 B2
(45) Date of Patent: Jul. 28, 2020

(54) METHOD FOR DETECTING TEST SUBSTANCE

(71) Applicant: SYSMEX CORPORATION, Kobe-shi, Hyogo (JP)

(72) Inventors: Kenji Akama, Kobe (JP); Hiroya Kirimura, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 187 days.

(21) Appl. No.: 16/034,638

(22) Filed: Jul. 13, 2018

(65) Prior Publication Data

US 2019/0025319 A1 Jan. 24, 2019

(30) Foreign Application Priority Data

Jul. 19, 2017 (JP) ................. 2017-140149

(51) Int. Cl.
*G01N 33/68* (2006.01)
*G01N 33/543* (2006.01)

(52) U.S. Cl.
CPC ....... *G01N 33/68* (2013.01); *G01N 33/54306* (2013.01); *G01N 33/54326* (2013.01); *G01N 2333/775* (2013.01)

(58) Field of Classification Search
None
See application file for complete search history.

(56) References Cited

U.S. PATENT DOCUMENTS 8,236,574 B2 * 8/2012 Duffy .............. G01N 33/54306
436/518
2007/0184433 A1 8/2007 Tao et al.

OTHER PUBLICATIONS

Silver et al. "Tethered-Based, Immune Sandwich Assay" (Biosens Bioelectron Jan. 15, 2015, p. 117-123). (Year: 2015).*

(Continued)

*Primary Examiner* — Changhwa J Cheu
(74) *Attorney, Agent, or Firm* — Sughrue Mion, PLLC

(57) ABSTRACT

Disclosed is a method for detecting a test substance, including a first contact step of bringing the test substance, a capturing body 1 that has binding properties to the test substance and is fixed to a substrate, and a capturing body 2 that has binding properties to the test substance and contains a label into contact with each other in a liquid to arrange at least a part of the capturing body 2 on the substrate; after the first contact step, a first dissociation step of dissociating a part of substances containing the capturing body 2 from the substrate and releasing it into the liquid; after the first dissociation step, a second contact step of bringing the test substance, the capturing body 1 that has binding properties to the test substance and is fixed to a substrate, and the capturing body 2 that has binding properties to the test substance and contains a label into contact with each other in the liquid to arrange at least a part of the capturing body 2 on the substrate; after the second contact step, a second dissociation step of dissociating a part of substances containing the capturing body 2 from the substrate and releasing it into the liquid; and a detection step of comparing a label-derived signal arrangement pattern on the substrate after dissociation in the first dissociation step with a label-derived signal arrangement pattern on the substrate after dissociation in the second dissociation step and detecting signals at substantially the same position as a signal indicating the test substance.

18 Claims, 11 Drawing Sheets

(56) References Cited

OTHER PUBLICATIONS

Akama et al. "Droplet-Free Digital Enzyme-Linked Immunosorbent Assay Based on a Tyramide Signal Amplification System" (Anal. Chem. 2016 88: 7123-7129). (Year: 2016).*

Emiel W.A. Visser et al., "Particle Motion Analysis Reveals Nanoscale Bond Characteristics and Enhances Dynamic Range for Biosensing", ACS Nano, 2016, pp. 3093-3101, vol. 10.

* cited by examiner

FIG. 12

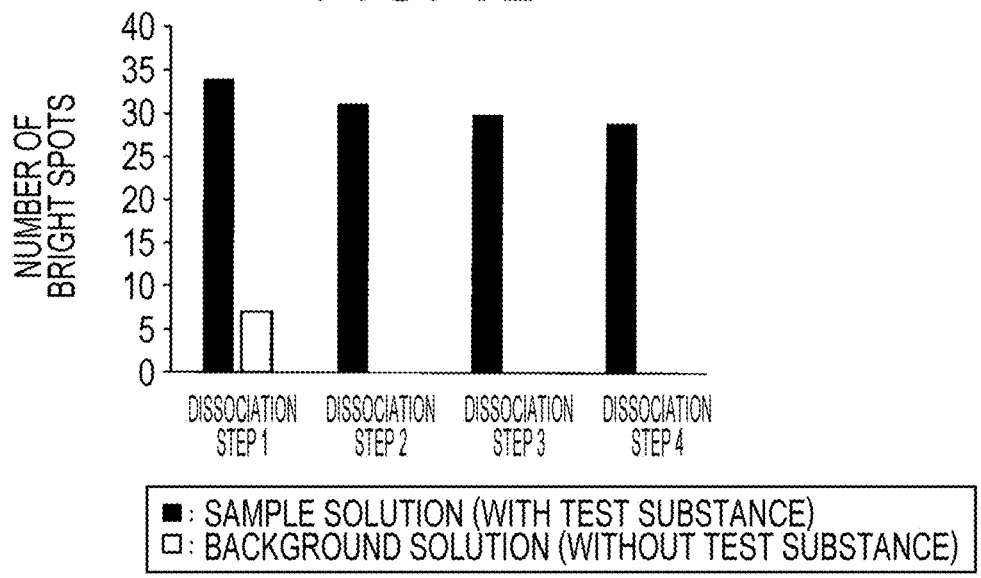

DISSOCIATION STEP 1: NUMBER OF BRIGHT SPOTS IN DISSOCIATION STEP 1

DISSOCIATION STEP 2: NUMBER OF BRIGHT SPOTS WITH UNCHANGED POSITIONS THROUGH DISSOCIATION STEPS 1 TO 2

DISSOCIATION STEP 3: NUMBER OF BRIGHT SPOTS WITH UNCHANGED POSITIONS THROUGH DISSOCIATION STEPS 1 TO 3

DISSOCIATION STEP 4: NUMBER OF BRIGHT SPOTS WITH UNCHANGED POSITIONS THROUGH DISSOCIATION STEPS 1 TO 4

FIG. 13

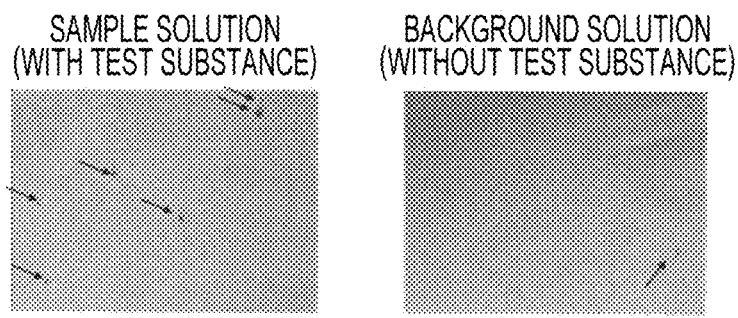

METHOD FOR DETECTING TEST SUBSTANCE

CROSS REFERENCE TO RELATED APPLICATIONS

This application claims priority from prior Japanese Patent Application No. 2017-140149, filed on Jul. 19, 2017, entitled "METHOD FOR DETECTING TEST SUBSTANCE", the entire contents of which are incorporated herein by reference.

TECHNICAL FIELD

The present invention relates to a method for detecting a test substance and the like.

BACKGROUND

Conventionally, a detection technique utilizing a specific binding reaction with a test substance is known. For example, in a detection technique called an ELISA method, a test substance is captured on a substrate by the substrate on which an antibody that specifically binds to a test substance is fixed, and further reacted with the antibody that specifically binds to the test substance to interpose the test substance between two antibodies, then an enzyme is bound thereto as a label to form an immunocomplex, and the test substance is detected by a signal based on the reaction of the enzyme and its substrate (US Patent Application Publication 2006/0188932).

SUMMARY

The scope of the present invention is defined solely by the appended claims, and is not affected to any degree by the statements within this summary.

However, such a detection method usually requires complicated work of separating a substance fixed on the substrate and a substance not fixed on the substrate (B/F separation). In addition, even when B/F separation is performed, nonspecific adsorption remains, which becomes the background of the signal, thus there has been a problem that the test substance cannot be specifically detected.

As a result of intensive research in view of the above problems, the present inventor has found that the problems can be solved by bringing a test substance, a capturing body 1 that has binding properties to the test substance and is fixed to a substrate, and a capturing body 2 that has binding properties to the test substance and contains a label into contact with each other in a liquid to arrange the capturing body 2 on the substrate, then repeating dissociation from the substrate and contact with the substrate of a substance containing the capturing body 2, comparing label-derived signal arrangement patterns on the substrate between a specific step and a specific step, and detecting signals at substantially the same position as a signal indicating the test substance (specific signal). As a result of advancing further research based on this finding, the present inventor has completed the present invention.

More specifically, the present invention includes the following aspects.

Item A

A method for detecting a test substance, including a first contact step of bringing the test substance, a capturing body 1 that has binding properties to the test substance and is fixed to a substrate, and a capturing body 2 that has binding properties to the test substance and contains a label into contact with each other in a liquid to arrange at least a part of the capturing body 2 on the substrate;

after the first contact step, a first dissociation step of dissociating a part of substances containing the capturing body 2 from the substrate and releasing it into the liquid;

after the first dissociation step, a second contact step of bringing the test substance, the capturing body 1 that has binding properties to the test substance and is fixed to a substrate, and the capturing body 2 that has binding properties to the test substance and contains a label into contact with each other in the liquid to arrange at least a part of the capturing body 2 on the substrate;

after the second contact step, a second dissociation step of dissociating a part of substances containing the capturing body 2 from the substrate and releasing it into the liquid; and a detection step of comparing a label-derived signal arrangement pattern on the substrate after dissociation in the first dissociation step with a label-derived signal arrangement pattern on the substrate after dissociation in the second dissociation step and detecting signals at substantially the same position as a signal indicating the test substance.

Item B

A method for detecting a test substance, including a first contact step of bringing the test substance, a capturing body 1 that has binding properties to the test substance and is fixed to a substrate, and a capturing body 2 that has binding properties to the test substance and contains a label into contact with each other in a liquid to arrange at least a part of the capturing body 2 on the substrate;

after the first contact step, a first dissociation step of dissociating a part of substances containing the capturing body 2 from the substrate and releasing it into the liquid;

after the first dissociation step, a second contact step of bringing the test substance, the capturing body 1 that has binding properties to the test substance and is fixed to a substrate, and the capturing body 2 that has binding properties to the test substance and contains a label into contact with each other in the liquid to arrange at least a part of the capturing body 2 on the substrate; and a detection step of comparing a label-derived signal arrangement pattern on the substrate after contact in the first contact step with a label-derived signal arrangement pattern on the substrate after contact in the second contact step and detecting signals at substantially the same position as a signal indicating the test substance.

Item C

An apparatus for detecting a test substance, including a reaction section for storing a reaction solution, the reaction solution containing the test substance and a capturing body 2 that has binding properties to the test substance and contains a label, and the bottom of the reaction section being a substrate on which a capturing body 1 having binding properties to the test substance is fixed;

an external force applying section for applying an external force to the capturing body 2;

an imaging section for imaging a label-derived signal arrangement pattern on the substrate; and a processing section for bringing the test substance, the capturing body 1 and the capturing body 2 into contact with each other in a liquid and adjusting an external force from the external force applying section so as to arrange at least a part of the capturing body 2 on the substrate, and after the contact, adjusting an external force from the external force applying section so as to dissociate a part of substances containing the capturing body 2 from the substrate and release it into the liquid, and comparing label-derived signal arrangement patterns during the contact and during the dissociation, and determining signals at substantially the same position during the contact and during the dissociation as a signal indicating the test substance.

Item D

An apparatus for detecting a test substance, including a reaction section having a substrate on which a capturing body 1 having binding properties to the test substance is fixed at the bottom and storing a reaction solution containing the test substance and a capturing body 2 having binding properties to the test substance and containing a label;

an external force applying section for applying an external force to the capturing body 2;

an imaging section for imaging a label-derived signal arrangement pattern on the substrate;

a control section for bringing the test substance, the capturing body 1 and the capturing body 2 into contact with each other in a liquid and adjusting an external force from the external force applying section so as to arrange at least a part of the capturing body 2 on the substrate, and after the contact, adjusting an external force from the external force applying section so as to dissociate a part of substances containing the capturing body 2 from the substrate to release it into the liquid, and a processing section for comparing label-derived signal arrangement patterns during the contact and during the dissociation, and determining signals at substantially the same position during the contact and during the dissociation as a signal indicating the test substance.

BRIEF DESCRIPTION OF THE DRAWINGS

FIG. 12 is a graph of the number of bright spots, showing the result of Example 1 (a comparison result between dissociation steps). ■ indicates the case of using a sample solution (with a test substance), and □ indicates the case of using a background solution (without a test substance). In the abscissa, dissociation step 1 shows the number of bright spots in dissociation step 1, dissociation step 2 shows the number of bright spots with unchanged positions through dissociation steps 1 and 2, dissociation step 3 shows the number of bright spots with unchanged positions through dissociation steps 1 to 3, and dissociation step 4 shows the number of bright spots with unchanged positions through dissociation steps 1 to 4;

FIG. 13 shows bright field images of the result of Comparative Example 1. An arrow indicates a bright spot.

DETAILED DESCRIPTION OF THE PREFERRED EMBODIMENTS

Figure 1:
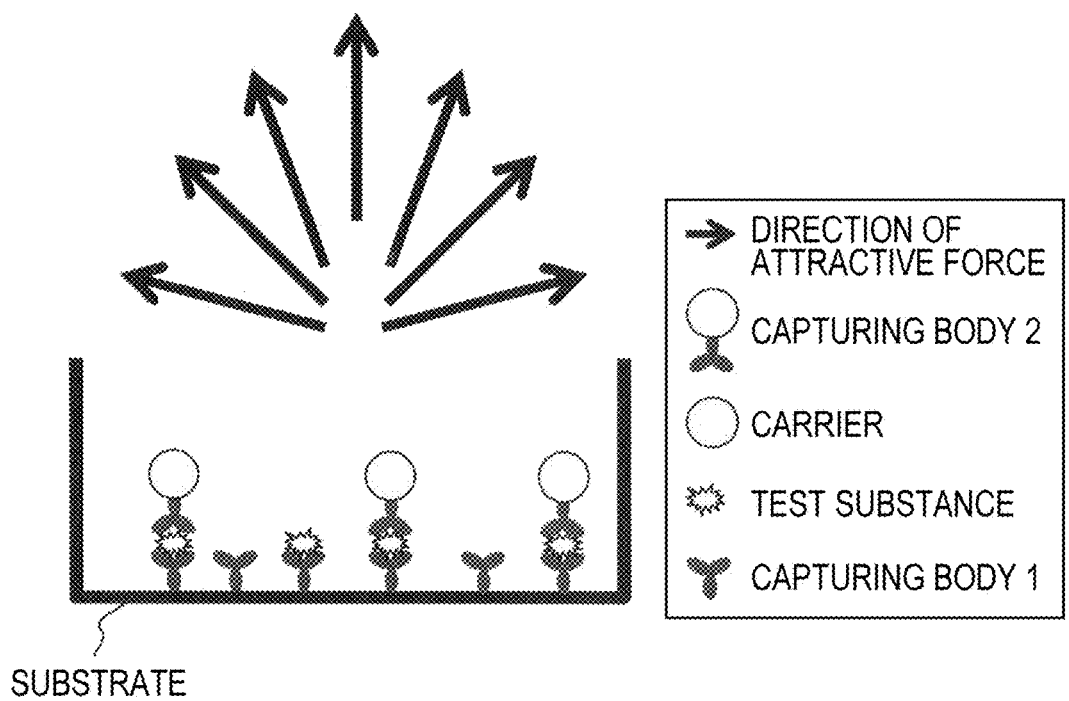
FIG. 1 is a schematic diagram showing an example of the direction of attractive force.

1. Method 1 for Detecting Test Substance

The present disclosure relates to, as one aspect thereof, a method for detecting a test substance, including a first contact step, a first dissociation step, a second contact step and a second dissociation step, and a detection step 1 (herein sometimes referred to as "detection method 1 of the present disclosure" in the specification). This will be described below.

1-1. First Contact Step

The first contact step is a step of bringing a test substance, a capturing body 1 that has binding properties to the test substance and is fixed to a substrate, and a capturing body 2 that has binding properties to the test substance and contains a label into contact with each other in a liquid to arrange at least a part of the capturing body 2 on the substrate.

The test substance is a substance to be detected in the detection method 1 of the present disclosure, and is not particularly limited as long as a substance having binding affinity to the test substance (herein sometimes referred to as "binding substance") exists, or a binding substance can be produced. When the binding substance is an antibody, any substance having antigenicity can be a test substance. Specific examples of the test substance include antibodies, proteins, nucleic acids, physiologically active substances, vesicles, bacteria, viruses, polypeptides, haptens, therapeutic drugs, metabolites of therapeutic drugs, and the like.

The number of amino acid residues of the polypeptide is not particularly limited, and the polypeptide includes not only proteins having a relatively large number of amino acid residues but also polypeptides having a relatively small number of amino acid residues, which are generally referred to as peptides or an oligopeptides.

Polysaccharides include not only those consisting only of sugar chains but also those which are bound to other molecules, for example, sugar chains present on a surface of cells or proteins, lipopolysaccharides which are an outer membrane component of bacteria, and the like.

Examples of the physiologically active substance include cell growth factors, differentiation-inducing factors, cell adhesion factors, enzymes, cytokines, hormones, sugar chains, lipids, and the like.

The vesicle is not particularly limited as long as they are vesicles composed of membranes, and includes vesicles that do not contain a liquid phase therein, those that contain a liquid phase therein, those that contain a mixed phase of a liquid phase and an oil phase therein, those that contain more minute vesicles therein, and the like. Examples of the vesicle include extracellular vesicles such as exosomes, microvesicles and apoptotic bodies, artificial vesicles such as liposomes, and the like.

The test substance may be one kind or a combination of two or more kinds.

The capturing body 1 is not particularly limited as long as it has binding properties to the test substance and is fixed to a substrate. The capturing body 1 may be composed of a single molecule or may be a complex composed of a plurality of molecules. It is preferable that the capturing body 1 has specific binding properties to the test substance.

The phrase "has binding properties" means that it is capable of reversibly or irreversibly binding to the test substance. The binding force is not particularly limited, and examples thereof include a hydrogen bond, an electrostatic force, a van der Waals force, a hydrophobic bond, a covalent bond, a coordinate bond, and the like. Although the binding degree is not particularly limited, for example, the dissociation constant between the test substance and the capturing body 1 is, for example, $1 \times 10^{-4}$ M to $1 \times 10^{-16}$ M, $1 \times 10^{-6}$ M to $1 \times 10^{-14}$ M, $1 \times 10^{-8}$ M to $1 \times 10^{-13}$ M, and $1 \times 10^{-9}$ M to $1 \times 10^{-12}$ M.

A site to which the capturing body 1 binds may be the same site as a site of the test substance to which the capturing body 2 binds described later, or may be a different site (including a case of overlapping and a case of not overlapping). Both sites are preferably different sites, and more preferably different sites which do not overlap. For example, when the capturing body 1 and the capturing body 2 are antibodies themselves or contain antibodies and the test substance is an antigen, it is preferably that an epitope of the test substance to which the capturing body 1 binds is different from an epitope of the test substance to which the capturing body 2 binds. As another example, when the capturing body 1 and the capturing body 2 are nucleic acids themselves or contain nucleic acids and the test substance is also a nucleic acid, a base sequence of the test substance to which the capturing body 1 binds is different from a base sequence of the test substance to which the capturing body 2 binds.

As used herein, the term "antibody" includes not only immunoglobulins such as polyclonal antibodies, monoclonal antibodies and chimeric antibodies, but also fragments having variable regions thereof, for example, Fab fragments, F(ab')2 fragments, Fv fragments, minibodies, scFv-Fc, scFv, diabodies, triabodies, and tetrabodies.

As used herein, the term "nucleic acid" includes not only DNA and RNA but also those subjected to known chemical modification, as exemplified below. In order to prevent degradation by hydrolases such as nucleases, a phosphoric acid residue (phosphate) of each nucleotide can be substituted with, for example, a chemically modified phosphoric acid residue such as phosphorothioate (PS), methylphosphonate, or phosphorodithionate. A hydroxyl group at the 2-position of sugar (ribose) of each ribonucleotide may be substituted with —OR (R represents, for example, CH3(2'-O-Me), CH2CH2OCH3(2'-O-MOE), CH2CH2NHC(NH)NH2, CH2CONHCH3, CH2CH2CN or the like). Further, a base moiety (pyrimidine, purine) may be chemically modified, and examples of the chemical modification include introduction of a methyl group or a cationic functional group to the 5-position of a pyrimidine base, substitution of a carbonyl group at the 2-position with thiocarbonyl, or the like. Furthermore, a phosphoric acid moiety and a hydroxyl moiety are modified with, for example, biotin, an amino group, a lower alkylamine group, an acetyl group, or the like, but it is not limited thereto. BNA (LNA) in which the conformation of sugar moiety is fixed to N-type by cross-linking the 2' oxygen and the 4' carbon of the sugar moiety of the nucleotide and the like can also be preferably used.

The capturing body 1 preferably contains "binding substance 1" which has binding properties to a test substance as a single substance. The binding substance 1 varies depending on the type of the test substance, and even the same test substance can be in various forms. For example, when the test substance is a substance having antigenicity, examples of the binding substance 1 include antibodies against the substance. When the test substance is an antibody, an antigen can be used as the binding substance 1. When the test substance is a nucleic acid, example of the binding substance 1 includes a nucleic acid capable of forming a strand complementary to the nucleic acid. When the test substance is a receptor or a ligand, example of the binding substance 1 includes a ligand or a receptor. Therefore, specific examples of the binding substance 1 include antibodies, antigens, nucleic acids, receptors, ligands that bind to receptors, aptamers, and the like. Besides this, a low molecular weight compound having binding properties to a specific molecule (for example, biotin, etc.) can also be adopted as the binding substance 1. The binding substance 1 may be one kind or a combination of two or more kinds.

In addition to the binding substance 1, the capturing body 1 may include a substance used for fixing to the substrate. Examples of such substances include proteins, antibodies, antigens, nucleic acids, receptors, ligands that bind to receptors, aptamers, low molecular weight compounds, and the like. The substance may be one kind or a combination of two or more kinds.

The substrate is not particularly limited as long as it can fix the capturing body 1. Examples of the substrate include substrates containing plastic such as polystyrene, glass or nitrocellulose as a main component. The form of the substrate is not particularly limited as long as it can hold a site (=liquid) where the test substance, the capturing body 1 and the capturing body 2 come into contact with each other. Specific examples of the substrate include the bottom of each well of the well plate, the bottom of a petri dish, and the like. The size of the well is not particularly limited, and includes from a size to contain one or several complexes of the test substance, the capturing body 1 and the capturing body 2 to a size of a normal microplate.

The phrase "fixed to a substrate" means that it is fixed by being directly or indirectly bound to a substrate. Fixation of the capturing body 1 to the substrate can be performed in accordance with or according to a conventional method. Specific mode of fixation is not particularly limited, and examples thereof include fixation via a covalent bond, fixation via binding of avidin or streptavidin to biotin, fixation by physical adsorption, and the like. Since the substrate is usually blocked with BSA or the like, the capturing body 1 may be fixed on the substrate via this blocking agent.

The capturing body 1 may be one kind or a combination of two or more kinds.

The capturing body 2 is not particularly limited as long as it has binding properties to a test substance and contains a label, and may be composed of a single molecule or a may be a complex composed of a plurality of molecules. It is preferable that the capturing body 2 has specific binding properties to a test substance.

As to the phrase "has binding properties", the description is the same as the above description concerning the capturing body 1.

The capturing body 2 preferably contains "binding substance 2" which has binding properties for a test substance as a single substance. As to the binding substance 2, the description is the same as the above description concerning the binding substance 1.

The label is not particularly limited as long as it can be made visible by a certain means so that each capturing body 2 can be recognized. As the label, for example, substances capable of binding to carrier particles having a size that can be visualized by enlarging with a microscope, a substance that itself emits a signal (for example, light such as fluorescence), a substance that emits a signal by reacting with other substance (for example, enzymes, etc.), and the like.

The average particle size of the carrier particles is not particularly limited, but is preferably a size that can be visualized by enlarging with a microscope. For example, the average particle size of the carrier particles is 1 nm to 10 μm, preferably 10 nm to 1 μm, and more preferably 50 nm to 500 nm. The average particle size of the carrier particles is a volume-based median diameter measured with a particle size distribution measuring device by laser diffraction/scattering method. Examples of the particle size distribution measuring device include "Microtrac MT3000 II" manufactured by NIKKISO CO., LTD., and the like. As used herein, the "particle size" means a diameter.

The material of the carrier particles is not particularly limited, and examples thereof include metal particles such as gold, silver, copper, iron, aluminum, nickel, manganese, titanium and oxides thereof; resin particles such as polystyrene and latex; silica particles; and the like. The shape of the carrier particles is not particularly limited, and examples thereof include a sphere, a rectangular parallelepiped, a cube, a triangular pyramid, and the like, or shapes close thereto. The carrier particles preferably have on the surface a substance for making binding of other substance (for example, binding substance 2, etc.) easier and/or stronger. Examples of such a substance include substances having a reactive group such as an epoxy group, an amino group, a carboxy group or an azide group; substances having affinity to other molecule such as avidin, protein A or protein B; and the like. The carrier particles are preferably magnetic particles, charged particles or the like, from the viewpoint that application of an external force described later becomes easier. Charged particles are charged carrier particles. The material of the particles is not particularly limited as long as it can impart charges among the above-mentioned materials. The carrier particles may further contain the following fluorescent substance. The carrier particles may be one kind or a combination of two or more kinds.

The fluorescent substance is not particularly limited, and examples thereof include fluorescein, rhodamine, Texas Red, tetramethylrhodamine, carboxyrhodamine, phycoerythrin, 6-FAM (trademark), Cy (registered trademark) 3, Cy (registered trademark) 5, Alexa Fluor (registered trademark) series, and the like. The fluorescent substance may be one kind or a combination of two or more kinds.

Examples of the enzyme include, but are not particularly limited to, β-galactosidase, alkaline phosphatase, glucose oxidase, peroxidase, polyphenol oxidase, and the like. The enzyme may be one kind or a combination of two or more kinds.

The label may be one kind or a combination of two or more kinds. For example, carrier particles containing a fluorescent substance, carrier particles having an enzyme fixed thereto or the like can be used.

It is preferable that the capturing body 2 contains carrier particles as described above as a label or separately from a label. Examples of the carrier particles preferably include magnetic particles, charged particles, and the like, from the viewpoint that application of an external force described later becomes easier as well as in the above.

The structure of the capturing body 2 is not particularly limited. For example, in the case where the capturing body 2 contains the binding molecule 2 and carrier particles, examples of the structure of the capturing body 2 include a structure in which one or a plurality of the binding molecules 2 directly or indirectly bound to the surface of carrier particles.

The test substance, the capturing body 1, and the capturing body 2 are usually brought into contact with each other in a solution. For example, it can be performed by adding a sample containing the test substance and a reagent containing the capturing body 1 to the substrate on which the capturing body 2 is fixed. The solution is usually a liquid using water as a main solvent. The liquid can be, for example, a buffer solution. Examples of the buffer solution include phosphate buffer, phosphate buffered saline, Tris buffer, HEPES buffer, borate buffer, acetate buffer, citrate buffer, and the like. Various additives may be contained in the liquid as long as they do not significantly inhibit the binding between the test substance 1 and the capturing bodies 1 and 2.

The mode of "bringing . . . into contact with each other in a liquid", when the first contact step is the first round of contact step, for example, it may be a mode in which the capturing body 1 is first brought into contact with the test substance, then the test substance binding to the capturing body 1 is sequentially brought into contact with the capturing body 2, or may be a mode in which the capturing body 1, the test substance and the capturing body 2 are simultaneously brought into contact with each other. Specific examples of the former (sequential contact mode) include a mode in which a liquid containing the test substance is added to a well to which the capturing body 1 is fixed so that at least a part of the test substance is bound to the capturing body 1, then a liquid containing the capturing body 2 is added. Specific examples of the latter (simultaneous contact mode) include a mode in which a liquid containing the test substance and the capturing body 2 (in the liquid, the test substance and the capturing body 2 may not be bound to each other or may be a partly bound to each other) is added to a well to which the capturing body 1 is fixed. In both of the sequential contact mode and the simultaneous contact mode, it is desirable that the contact time is sufficient, for example, 10 minutes to 3 hours, and preferably about 30 minutes to about 2 hours.

Examples of the mode of "bringing . . . into contact with each other in a liquid" include, when the first contact step is the second or subsequent round of contact step, a mode in which a factor (for example, an external force) of dissociating a part of substances containing the capturing body 2 from the substrate in the immediately preceding dissociation step is removed or weakened. That is, the contact step is in a state in which an external force weaker than the external force applied in the dissociation step is applied or a state in which no external force is applied. In this case, the time to remove or weaken the external force or the like is, for example, about 1 to 30 minutes, and preferably about 2 to 10 minutes.

The phrase "arrange . . . the capturing body 2 on the substrate" means that the capturing body 2 binds directly and/or indirectly onto the substrate (for example, via the capturing body 1, the test substance, or a complex thereof). That is, the phrase "arrange . . . the capturing body 2 on the substrate" includes not only when the capturing body 2 is arranged on the substrate based on specific binding to the test substance but also when the capturing body 2 is arranged on the substrate based on nonspecific binding (or adsorption).

1-2. First Dissociation Step

The first dissociation step is, after the first contact step, a step of dissociating a part of substances containing the capturing body 2 from the substrate and releasing it into the liquid.

The "substances containing the capturing body 2" dissociated from the substrate in this step may be only the capturing body 2 or a complex of the capturing body 2 and other substance. Examples of the complex include a complex of the capturing body 2 and a substance nonspecifically bound to the capturing body 2, and the like.

The phrase "a part of" substances containing the capturing body 2 means a part of the capturing bodies 2 among a plurality of "substances containing the capturing body 2" present on the substrate. When all the substances containing the capturing body 2 are dissociated, the positions of all the capturing bodies 2 are changed even through the second contact step has been done, and signals at the same positions cannot be detected in the detection step described later.

The dissociation method is not particularly limited as long as it is a method capable of dissociating a part of substances containing the capturing body 2 from the substrate and releasing it into the liquid. Examples of the dissociation method preferably include a method of adjusting the strength of an external force applied to the capturing body 2 arranged on the substrate, or applying the external force. Here, the external force refers to a force that attracts the capturing body 2 to the solution side with respect to the substrate. For example, when the capturing body 1 is fixed at the bottom of the substrate and a solution is present on the substrate, an external force (attractive force) for pulling the capturing body 2 to the upper side of the substrate is applied. This makes it possible to dissociate the substance containing the capturing body 2 from the substrate surface. The direction of the applied force is not particularly limited as long as the capturing body 2 dissociates from the substrate surface and is released into the solution. As illustrated in FIG. 1, when the horizontal direction of the substrate is set to 0 degrees, the direction of attractive force is not particularly limited as long as it is a direction toward the side where the capturing body 2 is present, for example, a direction larger than 0 degrees and smaller than 180 degrees. The direction is preferably a direction of 30 to 150 degrees, more preferably a direction of 60 to 120 degrees, and further preferably a direction of 80 to 100 degrees.

The type of the external force is not particularly limited and an appropriate external force can be selected irrespective of the type of the capturing body 2 or depending on the type of the capturing body 2. Examples of the external force include magnetic force, Coulomb force, centrifugal force, fluid force, light, sound wave, and the like, and preferably magnetic force, Coulomb force, sound wave, and the like. As a combination of the type of the capturing body 2 and the external force, for example, in the case where the capturing body 2 contains magnetic particles, magnetic force is preferably adopted. For example, in the case where the capturing body 2 contains charged particles, Coulomb force is preferably adopted. The external force may be one kind or a combination of two or more kinds.

As to adjustment of the strength of the external force, an adjustment from a state where a relatively weak external force is already applied can be performed by strengthening the external force, and an adjustment from a state where no external force is applied can be performed by applying a certain level or more external force. Specific examples of the method of adjusting the strength of the external force include, in the case of magnetic force, a method of bringing the magnet close to the substrate and a method of adjusting the magnetic force of the magnet fixed on the upper side of the substrate, and in the case of Coulomb force, a method of adjusting potentials of the electrodes arranged on the upper side and the lower side of the substrate. In the case of Coulomb force, the applied electric field may be unidirectional or alternating current. In the case of alternating current (Dielectrophoresis, DEP), particles may be uncharged particles with no charge.

In the case of using a magnet, the strength of the magnet is not particularly limited, and a magnet with an appropriate magnetic force can be adopted according to the types of the capturing body 2 and the test substance, the binding degree, and the like. As an example, the magnet may be a magnet having a magnetic flux density of, for example, 1 mT to 1000 T, preferably 10 mT to 100 T, more preferably 100 mT to 10 T, and further preferably 200 mT to 1 T.

The time for applying the external force for dissociation is not particularly limited as long as it is a time for which a part of substances containing the capturing body 2 is dissociated from the substrate, but it is, for example, 5 seconds to 5 minutes, preferably 10 seconds to 3 minutes, and more preferably from 20 seconds to 1 minute.

The phrase "dissociated from the substrate" means that the binding in which the substance containing the capturing body 2 is fixed on the substrate is dissociated. The phrase "dissociating . . . from the substrate and releasing it into the liquid" means that it is not in such a state that the "substance containing the capturing body 2" can be easily recombined on the substrate after dissociation. Specifically, for example, by continuing to apply an external force causing dissociation, it is possible to prevent the substance containing the capturing body 2 from recombining on the substrate.

It is preferable that the released "substance containing the capturing body 2" is present at a position as far apart from the substrate as possible. When the "substance containing the capturing body 2" is present in the vicinity of the substrate, in order to acquire a signal pattern on the substrate in the detection step described later, for example, when focusing on the vicinity of the substrate, a signal derived from the released "substance containing the capturing body 2" may also be detected, which is not preferable.

After a part of substances containing the capturing body 2 is released into the liquid, a signal arrangement pattern on the substrate is acquired. This pattern is used in the detection step 1 described later.

The "signal" is derived from the label of the capturing body 2. The signal is an optical signal corresponding to the type of label. When the label is a carrier particle having a certain size, for example, it is a spot observed in an enlarged image (either a bright field image or a dark field image). When the label is a fluorescent substance, it is, for example, a fluorescent bright spot observed in an enlarged image.

When the label is an enzyme, for example, it is a bright spot such as luminescence or fluorescence observed in an enlarged image after adding a substrate of the enzyme.

Figure 2:
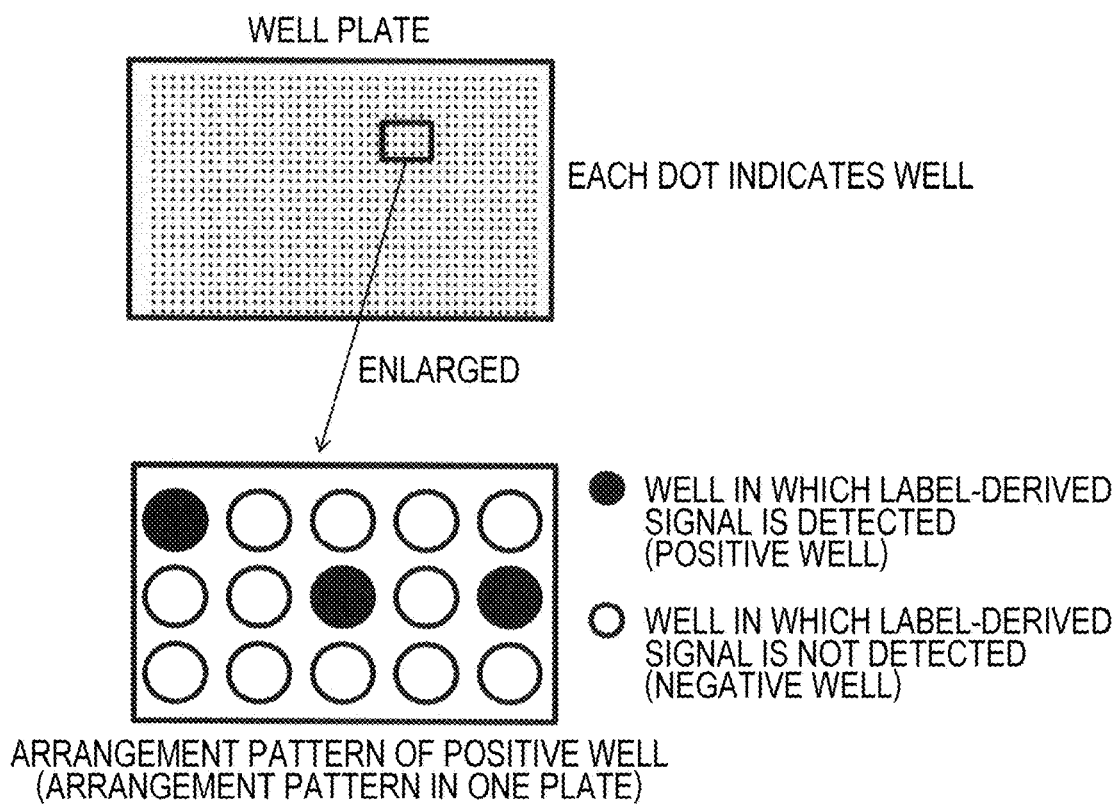
FIG. 2 is a schematic diagram showing an example of a case where a label-derived signal arrangement pattern is an arrangement pattern of a well (positive well) in which a label-derived signal is detected, which is formed on a well plate.

The phrase "signal arrangement pattern" includes information about where each signal is located on the substrate. When the substrate has a large number of minute partitions, it contains information on which partition a signal is generated. FIG. 2 shows an example of a signal arrangement pattern when a plate having a plurality of microwells is used. In the figure, a well indicated by black circle is "positive well" in which a signal is detected, and a well indicated by open circle is "negative well" in which a signal is not detected. The arrangement pattern of this positive well is the signal arrangement pattern in this example.

The label-derived signal arrangement pattern can be acquired by capturing an image (still image) and/or a moving image with appropriate imaging means under conditions in which label-derived signals can be observed. The imaging means is not particularly limited as long as it is capable of capturing a still image or a moving image, and examples thereof include CCD, CMOS, and the like.

In another embodiment, instead of capturing an image or a moving image, only the position information of the signal may be acquired as a signal arrangement pattern. For example, the signal arrangement pattern may be information including the number of signals on the substrate and the position (for example, coordinate information) of each signal.

1-3. Second Contact Step

The second contact step is, after the first dissociation step, a step of bringing the test substance, the capturing body 1 that has binding properties to the test substance and is fixed to a substrate, and the capturing body 2 that has binding properties to the test substance and contains a label into contact with each other in a liquid to arrange at least a part of the capturing body 2 on the substrate.

Except for the contents described below, the description regarding the second contact step is the same as the description of the first contact step.

Examples of the mode of "bringing . . . into contact with each other in a liquid" include a mode in which a factor of dissociating a part of substances containing the capturing body 2 from the substrate in the immediately preceding dissociation step (for example, an external force) is removed or weakened. In this case, the time to remove or weaken the external force or the like is, for example, about 1 to 30 minutes, and preferably about 2 to 10 minutes.

1-4. Second Dissociation Step

The second dissociation step is, after the second contact step, a step of dissociating a part of substances containing the capturing body 2 from the substrate and releasing it into the liquid.

The description regarding the second dissociation step is the same as the description of the first dissociation step.

1-5. Set of Other Contact Step and Dissociation Step

The detection method 1 of the present disclosure may include a contact step and a dissociation step before the first contact step. One or more contact steps and dissociation steps may be included between the first dissociation step and the second contact step. One or more contact steps and dissociation steps may be included between the second dissociation step and the detection step.

1-6. Detection Step 1

The detection step in the detection method 1 of the present disclosure (herein sometimes referred to as "detection step 1") is a step of comparing a label-derived signal arrangement pattern on the substrate after dissociation in the first dissociation step with a label-derived signal arrangement pattern on the substrate after dissociation in the second dissociation step and detecting signals at substantially the same position as a specific signal.

The detection of the specific signal is not particularly limited, and may be performed visually or may be performed through processing by CPU.

In the case of comparing based on the image (still image), the detection step 1 can be more specifically performed, for example, as follows.

An image P showing a signal arrangement pattern after dissociation in the first dissociation step and an image Q showing a signal arrangement pattern after dissociation in the second dissociation step are acquired.

The position of the label-derived signal in the image P is compared with the position of the label-derived signal in the image Q, and among the label-derived signals in the image Q, a label-derived signal at substantially the same position as the label-derived signal in the image P is detected as a specific signal.

The determination of signals at substantially the same position can also be performed, for example, as follows. An image (image 1) showing one label-derived signal arrangement pattern and an image (image 2) having the same visual field as the image 1 showing the other label-derived signal arrangement pattern are divided into a plurality of partitions based on the coordinate system, and compares whether or not a certain signal of the image 1 and a certain signal of the image 2 exist in the same partition. As a result, when both signals exist in the same partition, it can be determined that both are signals at substantially the same position. For example, in the example shown in FIG. 3, it can be determined that signal 1-1 and signal 2-1 are signals at substantially the same position, but it is determined that the signal 1-2, and signals 2-2 and 2-3 are not signals at substantially the same position.

As another example, the determination can also be performed as follows. In the image (image A) showing one label-derived signal arrangement pattern, the luminance center of gravity is determined based on the luminance distribution of the signal. Then, whether or not the signal in the image (image B) having the same visual field as the image 1 showing the other label-derived signal arrangement pattern exists within a predetermined range from the luminance center of gravity of the signal in the image A is compared. As a result, when the signal in the image B exists within the predetermined range from the luminance center of gravity of the signal in the image A, it can be determined that both are signals at substantially the same position. For example, in the example shown in FIG. 4, it can be determined that signal A and signal B-1 are signals at substantially the same position, but it is determined that the signal A and signal B-2 are not signals at substantially the same position.

Figure 3:
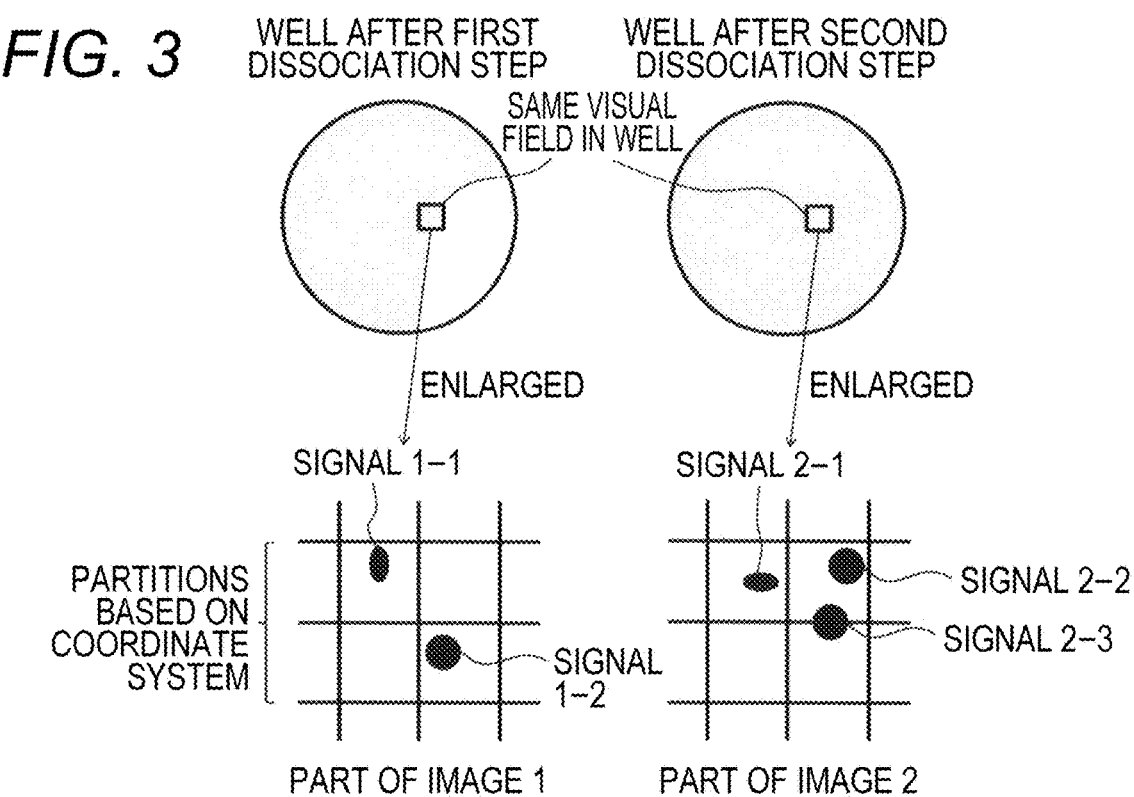
FIG. 3 is a schematic diagram showing an example of a method of determining signals at substantially the same position based on a partition by a coordinate system.
Figure 4:
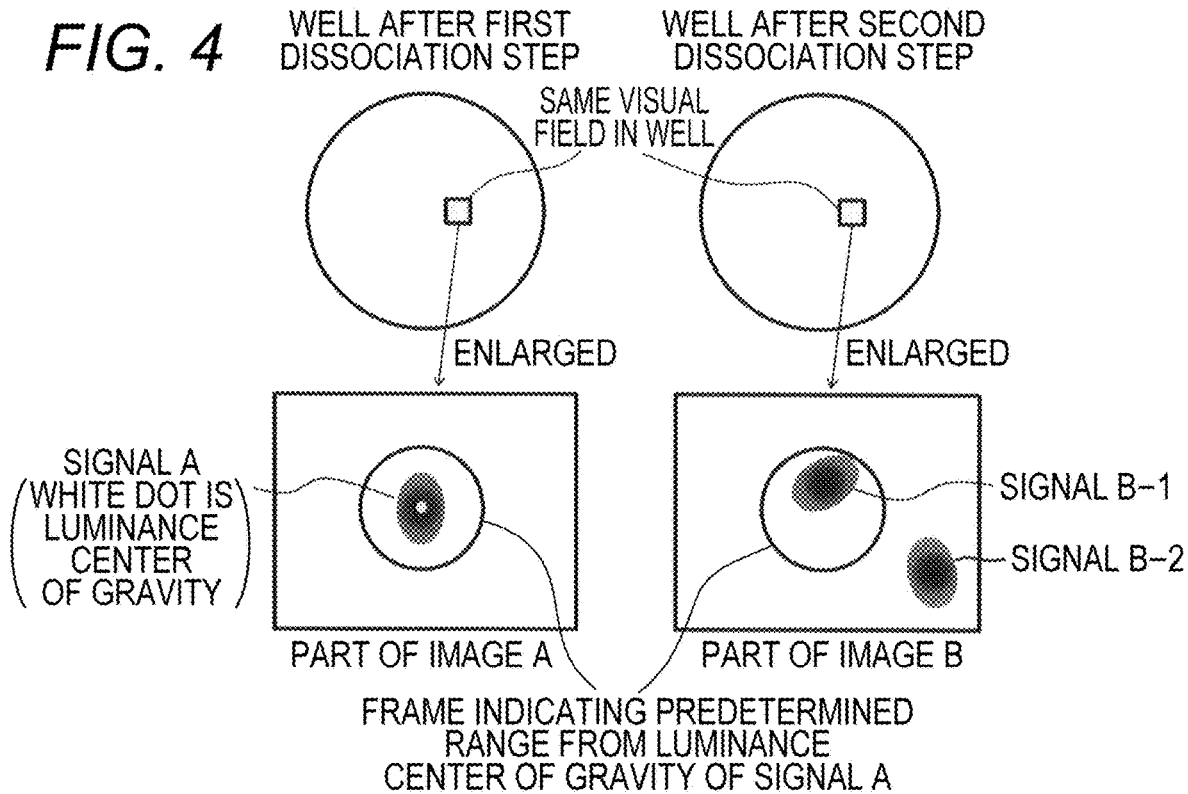
FIG. 4 is a schematic diagram showing an example of a method of determining signals at substantially the same position based on a predetermined range from the luminance center of gravity.

Like the capturing bodies 1 and 2 and the test substance, in the complex of molecules, the position may change slightly every time the image is captured even the same complex, due to rotation of a part of the complex (such as intermolecular binding moiety) or the like. Therefore, as shown in FIG. 3 and FIG. 4, it is preferable to determine signals not at exactly the same position as the signals detected in the image 1 and the image A but in the vicinity thereof also as signals at the same position.

Figure 5:
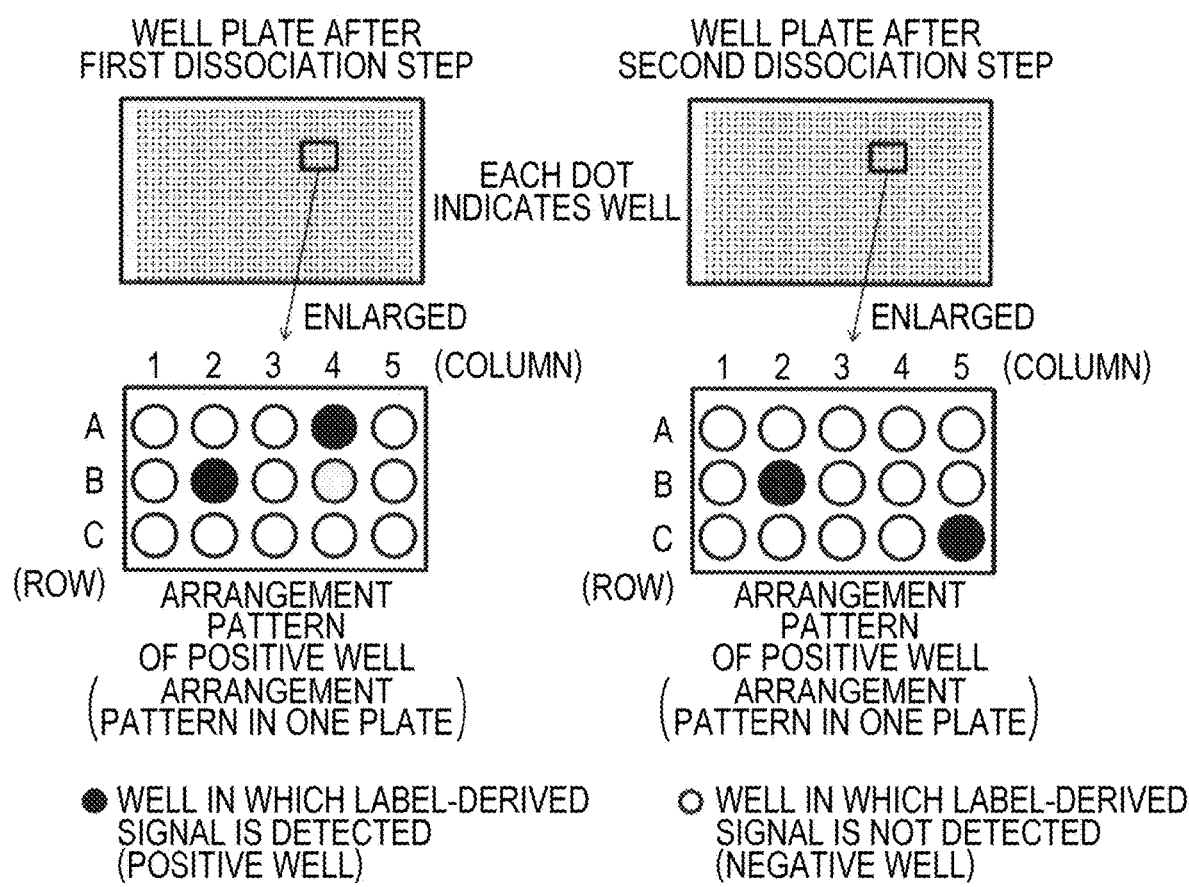
FIG. 5 is a schematic diagram showing an example of a method of determining signals at the same position based on a position on a plate of a positive well (well in which a signal was observed)

When a microwell is used, positive wells at the same position can be determined as signals at the same position. For example, in the example shown in FIG. 5, positive well in row 2, column B in the well plate after the first dissociation step and in the well plate after the second dissociation step can be determined as signals at the same position.

Signals at substantially the same position in the label-derived signal arrangement pattern on the substrate after dissociation in the first dissociation step and the label-derived signal arrangement pattern on the substrate after dissociation in the second dissociation step can be detected (or determined) as specific signals. When contact-dissociation is repeated three or more times in the detection method 1 of the present disclosure, signals at the same position in two or more dissociation steps can be determined as a signal (a specific signal) indicating the test substance. In another embodiment, when contact-dissociation is repeated three or more times, signals at the same position in all dissociation steps may be determined as specific signals.

On the other hand, signals other than specific signals can be detected as nonspecific signals.

In the case of comparing based on a moving image, more specifically, the detection step 1 can detect a specific signal, for example, as follows.

The signal arrangement patterns of the substrate at least in the first dissociation step and the second dissociation step are imaged.

It is a step of detecting a signal that is at substantially the same position from the first dissociation step to the second dissociation step in the moving image as a specific signal. The determination of "at substantially the same position" in this case can also be performed in accordance with or according to the above-mentioned example.

It is also possible to integrate the number or strength of specific signals and use the obtained integrated value as the amount of the test substance. In this case, it is also possible to determine the concentration based on the calibration curve.

It may be used as an index of the content of the test substance, based on the ratio of the specific signal among the whole signals (the sum of the specific signals and the nonspecific signals).

1-7. Example of Embodiment of Detection Method 1 of Present Disclosure

Figure 6:
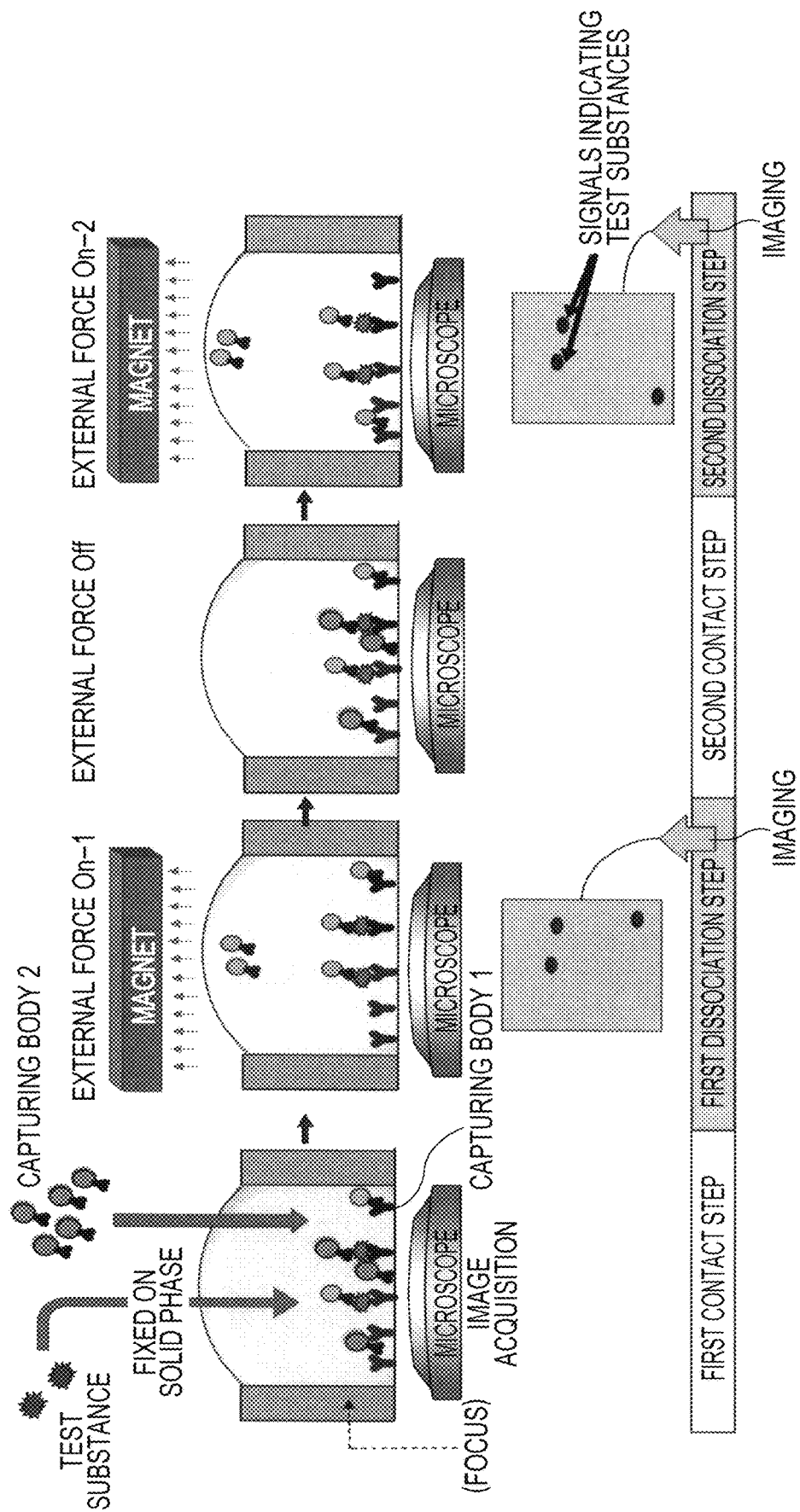
FIG. 6 is a schematic diagram showing an example of an embodiment of detection method 1 (an example of using magnetic particles as carrier particles)

The principle of the detection method 1 of the present disclosure will be described with reference to an example of the embodiment of the detection method 1 of the present disclosure in FIG. 6. FIG. 6 shows a case where magnetic particles are used as carrier particles having capturing body 2.

In a first contact step, capturing body 1 fixed to a substrate, capturing body 2 composed of an antibody and magnetic particles and a test substance are brought into contact with each other. Accordingly, the capturing body 2 is arranged on the substrate via specific binding to the test substance. On the other hand, a part of the capturing bodies 2 nonspecifically bind to a substance other than the test substance (substrate surface, capturing body 1 or the like).

Subsequently, in a first dissociation step, attractive force is applied to the capturing body 2 (including the magnetic particles) by arranging a magnet on the upper side of the substrate. Accordingly, the capturing body 2 arranged on the substrate by relatively weak binding (usually nonspecific binding to a substance other than the test substance) is dissociated from the substrate and released into a liquid. At this point, an arrangement pattern of signals (black dots in the image of each step in FIG. 6) derived from the labels of the capturing bodies 2 is imaged focusing around the substrate.

Subsequently, in a second contact step, the attractive force to the capturing body 2 (including the magnetic particles) is removed by removing the magnet from the upper side of the substrate. Accordingly, the capturing body 2 that has been released can contact with the substance and the like on the substrate again. It is considered that the capturing body 2 is moved during release (for example, moved by Brownian motion or the like), and when a part of the capturing bodies 2 nonspecifically bind, the capturing body 2 is probablistically arranged at a position different from the position on the substrate during the first contact step.

Subsequently, in a second dissociation step, attractive force is applied to the capturing body 2 (including the magnetic particles) by arranging a magnet on the upper side of the substrate again. Accordingly, the capturing body 2 arranged on the substrate by relatively weak binding (usually nonspecific binding to a substance other than the test substance) is dissociated from the substrate and released into the liquid. At this point, an arrangement pattern of signals (black dots in the image of each step in FIG. 6) derived from the labels of the capturing bodies 2 is imaged focusing around the substrate.

It is considered that the capturing body 2 released in the first dissociation step has been arranged on the substrate by relatively weak binding, that is, nonspecific binding. It is considered that, even when not released in the first dissociation step, the capturing body 2 released in the second dissociation step was also arranged on the substrate by relatively weak binding, that is, nonspecific binding. Therefore, signals derived from the labels of the capturing bodies 2 that have not been released in both of the first dissociation step and the second dissociation step, that is, signals at substantially the same position in the first dissociation step and the second dissociation step can be detected as a signal indicating the test substance.

Figure 7:
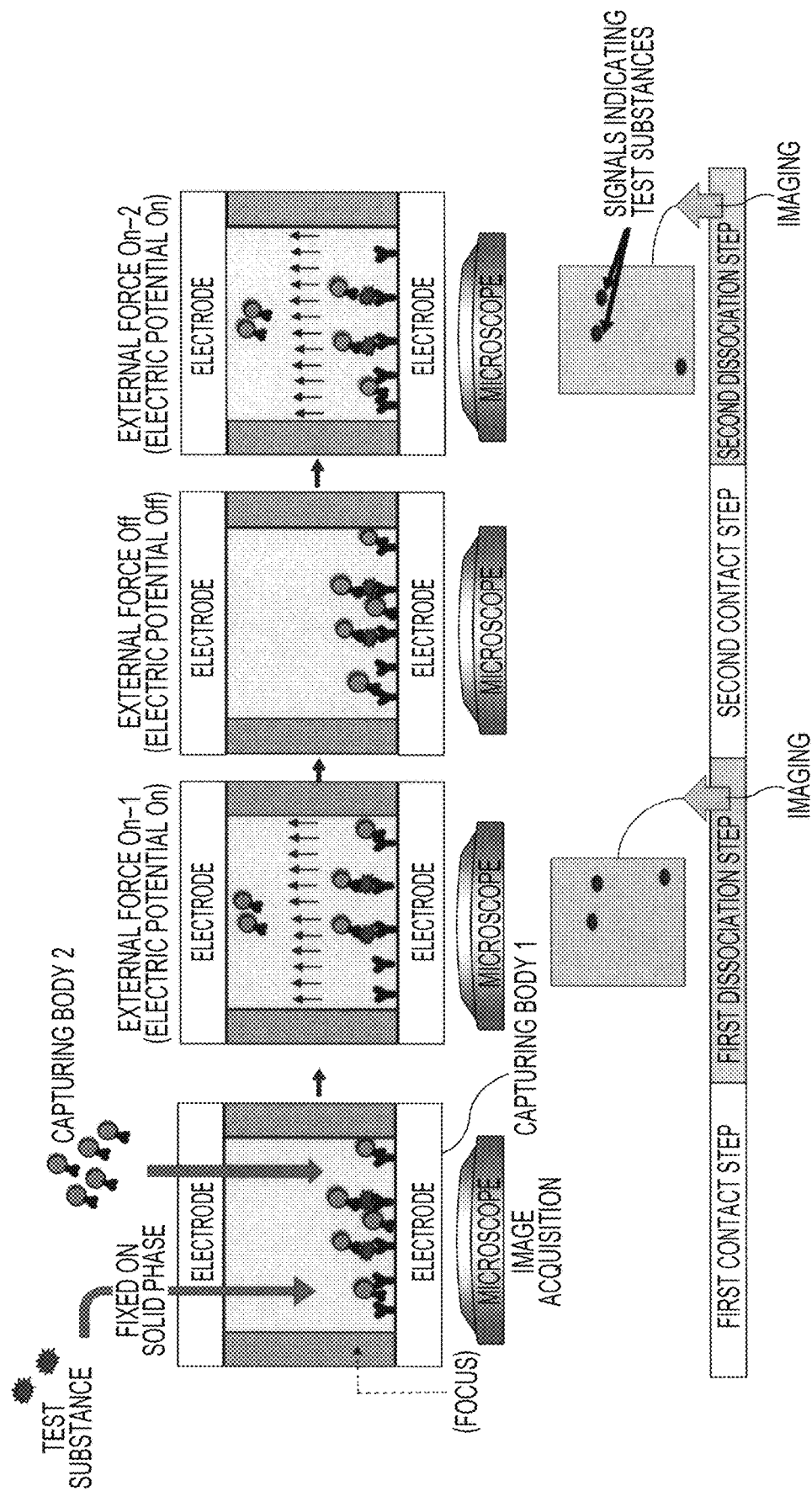
FIG. 7 is a schematic diagram showing an example of an embodiment of detection method 1 (an example of using charged particles as carrier particles)

FIG. 7 is shown as another example of the embodiment of the detection method 1 of the present disclosure. FIG. 7 shows a case where charged particles are used as carrier particles contained in the capturing body 2. In this embodiment, electrodes are provided on the upper side and the lower side of the substrate. The upper and lower electrodes are in contact with a liquid containing the capturing body 2 in at least a part thereof. In the dissociation step, for example, when the charged particle is a particle having a positive charge, an electric potential is applied to the electrodes to set the electrode on the upper side of the substrate to a negative electric potential and the electrode on the lower side of the substrate to a positive electric potential. Accordingly, attractive force and repulsive force for directing toward the upper side of the substrate are applied to the capturing body 2. On the other hand, when the charged particle is a particle having a negative potential, attractive force and repulsive force for directing toward the upper side of the substrate are applied to the capturing body 2 by reversing the positive and negative of the two electrodes. In the contact step, by stopping the potential application to the electrodes, the capturing body 2 that has been released can contact with the substance and the like on the substrate again. Regarding other than the above, the description of FIG. 7 is the same as the description of FIG. 6. The applied electric field may be unidirectional or alternating current. In the case of alternating current (Dielectrophoresis, DEP), unlike the embodiment of FIG. 7 employing charged particles as carrier particles, it may be an embodiment employing uncharged particles with no charge as carrier particles.

2. Method 2 for Detecting Test Substance

The present disclosure relates to, as one aspect thereof, a method for detecting a test substance, including a first contact step, a first dissociation step and a second contact step, and detection step 2 (herein sometimes referred to as "detection method 2 of the present disclosure" in the specification). This will be described below.

Other than the contents described below, the description regarding the detection method 2 of the present disclosure is the same as the description of the detection method 1 of the present disclosure.

In the first contact step and the second contact step, at least a part of the capturing body 2 is arranged on the substrate, and then a label-derived signal arrangement pattern on the substrate is acquired. This pattern is used in the detection step 2 described later. In the detection method 2 of the present disclosure, unlike the detection method 1 of the present disclosure, acquisition of the disposition pattern in the first dissociation step is not required.

The detection step in the detection method 2 of the present disclosure (herein sometimes referred to as "detection step 2") is a step of comparing a label-derived signal arrangement pattern on the substrate after contact in the first contact step with a label-derived signal arrangement pattern on the substrate after contact in the second contact step and detecting signals at substantially the same position as a signal indicating the test substance. Comparison of arrangement patterns and determination of signals at substantially the same position can be performed in the same manner as the detection method 1.

The principle of the detection method 2 of the present disclosure is as follows. It is considered that the capturing body 2 released in the first dissociation step has been arranged on the substrate by relatively weak binding, that is, nonspecific binding. The capturing body 2 released in the first dissociation step can contact with the substance and the like on the substrate again in the second contact step, but it is considered that the capturing body 2 is moved during release (for example, moved by Brownian motion or the like), so that it is arranged at a position different from the position on the substrate during the first contact step via specific or nonspecific binding. Therefore, signals derived from the labels of the capturing bodies 2 that have not been released in the first dissociation step, that is, signals at substantially the same position in the first contact step and the second contact step can be detected as a signal indicating the test substance.

3. Apparatus for Detecting Test Substance

The present disclosure relates to, in one aspect thereof, an apparatus for detecting a test substance, including a reaction section, an external force applying section, an imaging section, and a processing section (herein sometimes referred to as "detection apparatus of the present disclosure"). The detection methods 1 and 2 of the present disclosure can be performed by, for example, the detection apparatus of the present disclosure. Hereinafter, the detection apparatus of the present disclosure will be described with reference to the accompanying drawings, but the detection apparatus of the present disclosure is not limited to only this embodiment. In the detection apparatus of the present disclosure, explanation of the terms already explained for the detection methods 1 and 2 of the present disclosure is omitted, but the explanation of each term in the detection methods 1 and 2 of the present disclosure is also applied to the detection apparatus of the present disclosure.

3-1. Configuration of Apparatus

Figure 8:
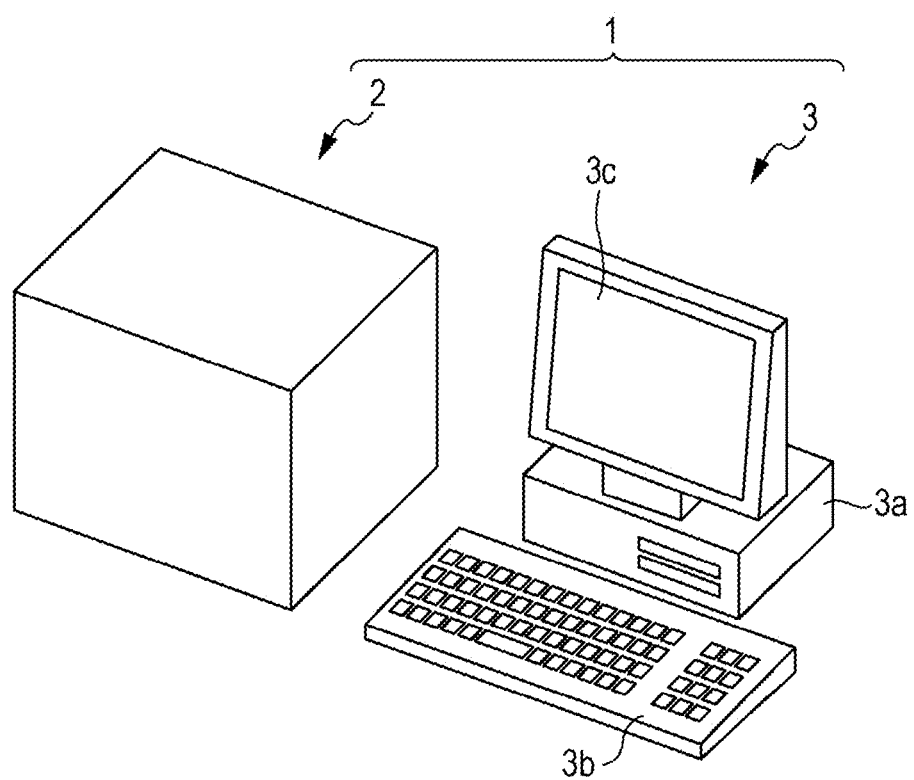
FIG. 8 is a schematic view showing a configuration of an embodiment of detection apparatus.

FIG. 8 is a schematic view showing a configuration of an embodiment of the detection apparatus (detection apparatus 1) of the present disclosure.

The detection apparatus 1 shown in FIG. 8 includes a measuring device 2 including a reaction section, an external force applying section, and an imaging section. The reaction section has a substrate on which capturing body 1 having binding properties to the test substance is fixed at the bottom and stores a reaction solution containing the test substance and capturing body 2 having binding properties to the test substance and containing a label. The external force applying section applies an external force to the capturing body 2. The imaging section images a label-derived signal arrangement pattern on the substrate. Optical information such as an image showing the label-derived signal arrangement pattern is transmitted to a computer system 3.

As the measuring device 2, for example, a microscope including an external force applying section and an imaging section can be used. In this case, each well of the well plate, petri dish or the like to be installed on the stage of the microscope is the reaction section.

The microscope is not particularly limited as long as it has a resolution capable of recognizing each of the label-derived signals, and an appropriate microscope can be adopted, according to the type of the label and the detection method of the label-derived signal. Specific examples of the microscope include optical microscopes such as stereomicroscope, fluorescent microscope, laser-scanning microscope, and confocal laser microscope; electron microscopes such as transmission electron microscope and scanning electron microscope; scanning probe microscopes such as atomic force microscope, scanning tunnel microscope, and scanning near field optical microscope; X-ray microscope; ultrasonic microscope; and the like.

The imaging section is arranged in a position that can capture an observation image of the microscope, for example, an eyepiece lens unit, a photograph straight tube, a C mount, or the like. The imaging section is not particularly limited as long as it can capture a still image or a moving image, and examples thereof include a digital camera, an analog camera, a digital video camera, an analog video camera, and the like.

The external force applying section is arranged at a portion where the capturing body 2 can be dissociated from the substrate by an external force. In this mode, an appropriate mode can be appropriately selected by a method of adjusting an external force. For example, when the external force is adjusted by approaching a magnet and the substrate, a magnet that is operable (for example, vertically and/or horizontally operable) as necessary is arranged on the upper side of the substrate. As another example, when the external force is adjusted by adjusting the magnetic force of the magnet fixed to the upper side of the substrate, a magnet whose magnetic force can be adjusted by a current is arranged on the upper side of the substrate. As another example, when the external force is adjusted by adjusting the potential of the electrode, an electrode whose potential can be adjusted by a current is arranged on the upper side and the lower side of the substrate so as to enable to contact with the liquid containing the capturing body 2.

The detection apparatus 1 shown in FIG. 8 includes a computer system 3 including a processing section, which is connected to the measuring device 2 directly or via a network.

The processing section,
brings the test substance, the capturing body 1 and the capturing body 2 into contact with each other in a liquid and adjusting an external force from the external force applying section so as to arrange at least a part of the capturing body 2 on the substrate, and after the contact, adjusts an external force from the external force applying section so as to dissociate a part of substances containing the capturing body 2 from the substrate and release it into the liquid, and compares label-derived signal arrangement patterns during the contact and during the dissociation, and determines signals at substantially the same position during the contact and during the dissociation as a signal indicating the test substance.

The computer system 3 includes a computer main unit 3a, an input device 3b, and a display unit 3c that displays specimen information, results, and the like. The computer system 3 receives optical information such as an image showing a label-derived signal arrangement pattern from the measuring device 2. Then, the processor of the computer system 3 executes a program for determining a signal indicating the test substance based on the optical information.

Figure 9:
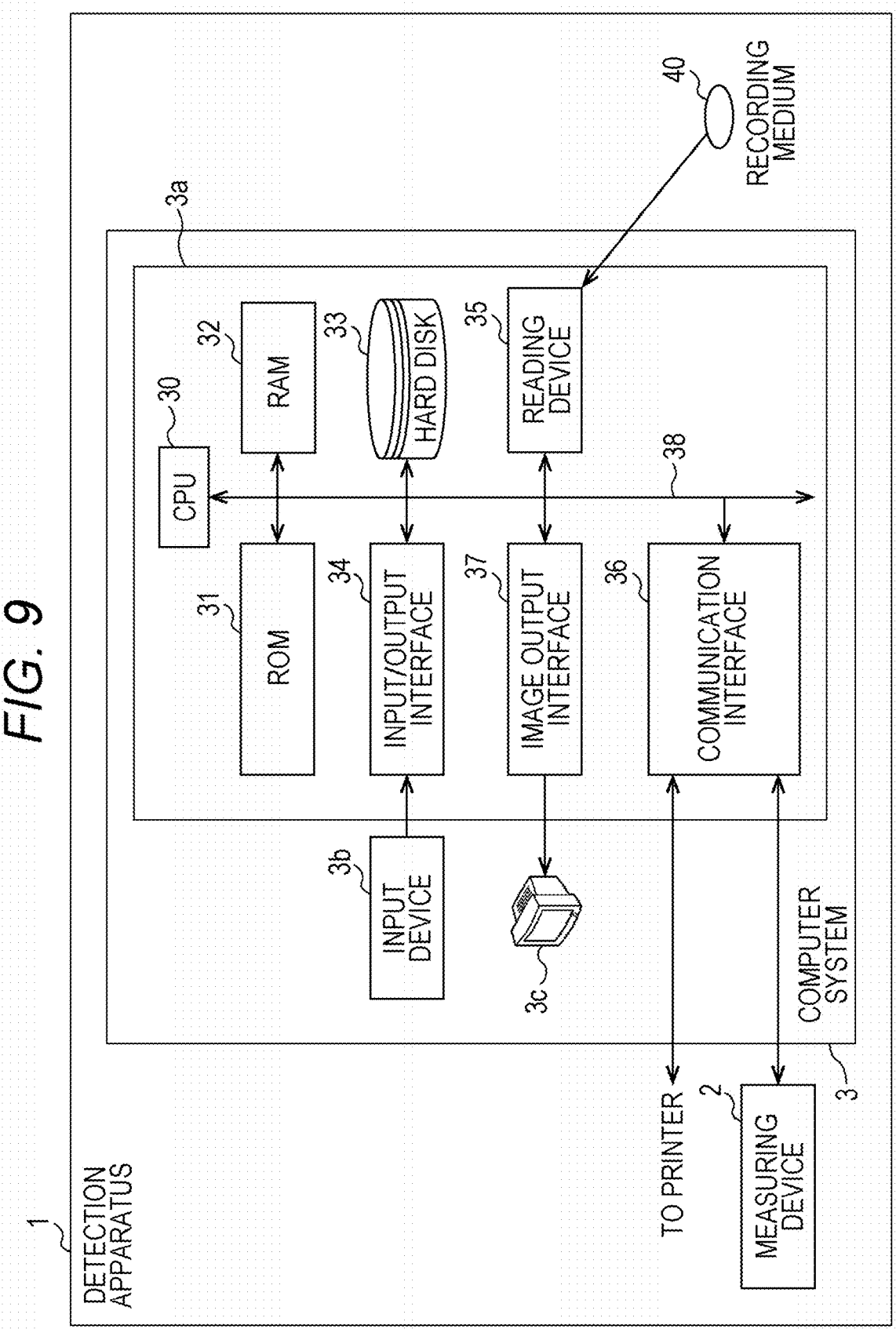
FIG. 9 is a block diagram showing a hardware configuration of the detection apparatus shown in FIG. 8.

FIG. 9 is a block diagram showing a hardware configuration of the detection apparatus shown in FIG. 8.

As shown in FIG. 9, the computer main body 3a includes a processing section (CPU (Central Processing Unit)) 30, a ROM (Read Only Memory) 31, a RAM (Random Access Memory) 32, a hard disk 33, an input/output interface 34, a reading device 35, a communication interface 36, and an image output interface 37. The processing section (CPU) 30, the ROM 31, the RAM 32, the hard disk 33, the input/output interface 34, the reading device 35, the communication interface 36 and the image output interface 37 are data-communicably connected by a bus 38.

The processing section (CPU) 30 can execute a computer program stored in the ROM 31 and a computer program loaded in the RAM 32. The processing section (CPU) 30 executes an application program, whereby the processing section (CPU) 30 functions as a terminal as an apparatus for determining a signal indicating the test substance.

The ROM 31 includes a mask ROM, PROM, EPROM, EEPROM, and the like. In the ROM 31, a computer program executed by the processing section (CPU) 30 and data used therefor are recorded.

The RAM 32 includes SRAM, DRAM, and the like. The RAM 32 is used for reading the computer program recorded in the ROM 31 and the hard disk 33. The RAM 32 is also used as a work area of the processing section (CPU) 30 when executing these computer programs.

The hard disk 33 has installed therein an operating system to be executed by the processing section (CPU) 30, a computer program such as an application program (the computer program for determining a signal indicating a test substance), and data used for executing the computer program.

The reading device 35 is constituted of a flexible disk drive, a CD-ROM drive, a DVD-ROM drive, and the like. The reading device 35 can read a computer program or data recorded on a portable recording medium 40.

The input/output interface 34 includes, for example, a serial interface such as USB, IEEE1394 and RS-232C, a parallel interface such as SCSI, IDE and IEEE1284, and an analog interface including a D/A converter, an A/D converter and the like. The input device 3b such as a keyboard and a mouse is connected to the input/output interface 34. The operator can input data to the computer main unit 3a by using the input device 3b.

The communication interface 36 is, for example, an Ethernet (registered trademark) interface or the like. The computer system 3 can transmit print data to a printer through the communication interface 36.

The image output interface 37 is connected to the display unit 3c constituted of an LCD, a CRT, and the like. Accordingly, the display unit 3c can output the video signal corresponding to the image data given from the processing section (CPU) 30. The display unit 3c displays an image (screen) according to the inputted video signal.

3-2. Operation of Apparatus

Figure 10:
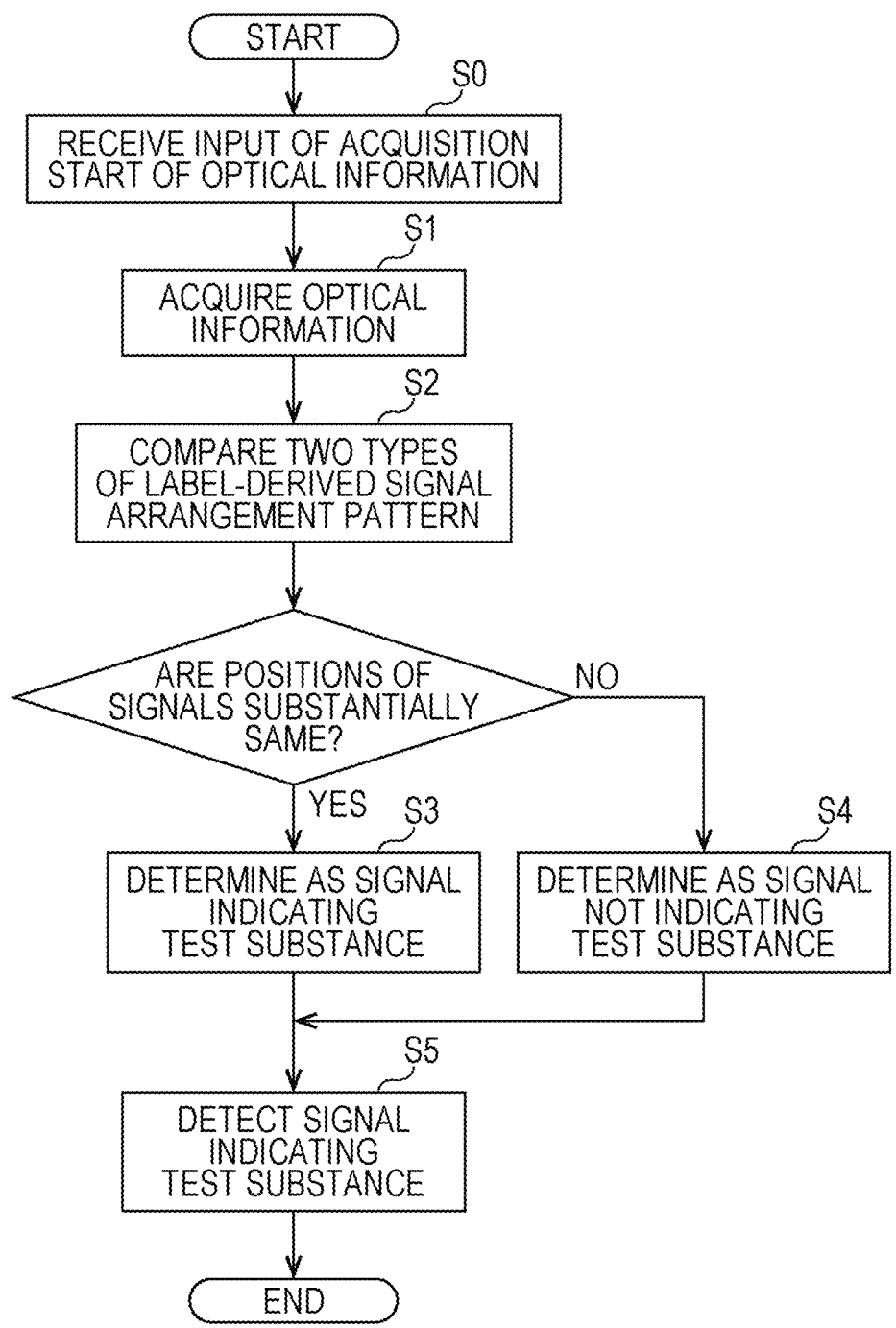
FIG. 10 is a diagram showing an operation of a processing section.

Next, the operation of the detection apparatus of the present disclosure will be described with reference to FIG. 10. The operation of the detection apparatus of the present disclosure is controlled by the processing section (CPU) 30 of the computer system 3.

Initially, the processing section 30 brings the test substance, the capturing body 1 and the capturing body 2 into contact with each other in a liquid, and adjusts an external force from the external force applying section so as to arrange at least a part of the capturing body 2 on the substrate, and after the contact, adjusts an external force from the external force applying section so as to dissociate a part of substances containing the capturing body 2 from the substrate and release it into the liquid. This set of contact and dissociation is carried out plural times as necessary.

Next, the processing section 30 receives an input for starting acquisition of optical information such as an image showing a label-derived signal arrangement pattern generated by the measuring device 2, with respect to the computer main body 3a performed by the inspector from the input device 3b (Step S0).

Subsequently, the processing section 30 acquires optical information such as an image showing a label-derived signal arrangement pattern generated by the measuring device 2 (Step S1). At this time, two types of label-derived signal arrangement patterns, specifically, the arrangement pattern of the first dissociation step and the arrangement pattern of the second dissociation step, or the arrangement patterns of the first contact step and the second contact step are acquired. The arrangement patterns may be acquired simultaneously or acquired separately.

Subsequently, the processing section 30 compares the two types of label-derived signal arrangement patterns acquired in Step S1 (Step S2). Specifically, the position of each signal is compared between the two types of label-derived signal arrangement patterns. As a result of the comparison, signals at substantially the same position in the two types of label-derived signal arrangement patterns are determined as a signal indicating the test substance (Step S3), and signals which are not at substantially the same position are determined as a signal not indicating the test substance (Step S4).

More specific aspects of this comparison and determination are, for example, as follows. An image (image 1) showing one label-derived signal arrangement pattern and an image (image 2) having the same visual field as the image 1 showing the other label-derived signal arrangement pattern are divided into a plurality of partitions based on the coordinate system, and compares whether or not a certain signal of the image 1 and a certain signal of the image 2 exist in the same partition. As a result, when both signals exist in the same partition, it can be determined that both are signals at substantially the same position.

Another example of a more specific aspect of this comparison and determination is as follows. In the image (image A) showing one label-derived signal arrangement pattern, the luminance center of gravity is determined based on the luminance distribution of the signal. Then, whether or not the signal in the image (image B) having the same visual field as the image 1 showing the other label-derived signal arrangement pattern exists within a predetermined range from the luminance center of gravity of the signal in the image A is compared. As a result, when the signal in the image B exists within the predetermined range from the luminance center of gravity of the signal in the image A, it can be determined that both are signals at substantially the same position.

Another example of a more specific aspect of this comparison and determination is as follows. This example is an example of using a well plate having a plurality of wells of a size to contain one complex of the test substance, the capturing body 1, and the capturing body 2. In this example, it can be said that the well (positive well) in which the label-derived signal is detected is the label-derived signal itself. Therefore, the position on the plate of the positive well (well in which a signal was observed) in one label-derived signal arrangement pattern and the position on the plate of the positive well (well in which a signal was observed) in the other label-derived signal arrangement pattern. As a result, when both are at the same position on the plate, it can be determined that both are signals at the same position.

A signal determined to indicate a test substance is detected as a test substance (Step S5).

The processing section 30 can output the information of Steps S1 to S5 from the display unit 3c via the image output interface 37. The processing section 30 may record the information on the recording medium 40 or the like.

Steps S1 to S5 are executed by a computer program. The computer program may be stored in a semiconductor memory element such as a hard disk or a flash memory, or a storage medium such as an optical disk. The storage format of the program in the storage medium is not limited as long as the presentation apparatus can read the program. Storage into the storage medium is preferably nonvolatile.

3-3. Other Aspects of Apparatus for Detecting Test Substance

The present disclosure also relates to, in one aspect thereof, an apparatus including a reaction section, an external force applying section, an imaging section, a control section, and a processing section.

In the present aspect, the control section brings the test substance, the capturing body 1 and the capturing body 2 into contact with each other in a liquid, and adjusts an external force from the external force applying section so as to arrange at least a part of the capturing body 2 on the substrate, and after the contact, adjusts an external force from the external force applying section so as to dissociate a part of substances containing the capturing body 2 from the substrate and release it into the liquid. The control section is provided in the measuring device 2, and the configuration thereof can adopt the same configuration as that of the computer system 3.

In the present aspect, the processing section compares label-derived signal arrangement patterns during the contact and during the dissociation, and determines signals at substantially the same position during the contact and during the dissociation as a signal indicating the test substance. Regarding the configuration of the processing section, the explanation in the above 2-1 is applied.

EXAMPLES

Hereinafter, the present disclosure will be described in detail based on examples, but the present disclosure is not limited to these examples.

Example 1 Detection of ApoA1

1-1. Contact Step 1
1-1-1. Preparation of Capturing Body 1

Through holes having a diameter of 5 mm were formed in a silicone rubber sheet (SR-50, thickness 5 mm, manufactured by TIGERS POLYMER CORPORATION), and the obtained sheet was attached to MAS coated glass (manufactured by Matsunami Glass Ind., Ltd.) to prepare wells on a glass substrate. Biotin was bound to BSA (manufactured by Proliant Biologicals, #68700) in accordance with a conventional method to obtain biotin-bound BSA. 0.5 µL of a 30 µg/mL biotin-bound BSA/PBS solution was added dropwise to the wells, and the wells were allowed to stand at room temperature for 1 hour. 50 µL of HISCL washing solution (manufactured by Sysmex Corporation) was added dropwise to the wells, and the wells were washed by pipetting. This washing operation was performed three times in total (hereinafter, three times of washing is simply referred to as "washing operation"). 50 µL of a 1% BSA/PBS solution was added dropwise to the wells, and the wells were allowed to stand overnight at 4° C., then washing operation was performed. 20 µL of a 10 µg/mL streptavidin/1% BSA/PBST solution was added dropwise to the wells, and the wells were allowed to stand at room temperature for 1 hour, then washing operation was performed. Meanwhile, an antibody solution to a test substance was prepared by diluting biotin-labeled Anti ApoA1 Antibody P1A5 (manufactured by Sysmex Corporation) to 10 µg/mL with StartingBloc (registered trademark) (PBS) Blocking Buffer (manufactured by Thermo Fisher Scientific). 10 µL of the antibody solution was added to the wells, and the wells were allowed to stand at room temperature for 1 hour, then washing operation was performed. By the above operation, a capturing body 1 having binding properties to the test substance (ApoA1) and fixed to the substrate (bottom of the well) was obtained.

1-1-2. Arrangement of Test Substance on Substrate

ApoA1, human recombinant (manufactured by Sigma Aldrich) was diluted to 1 µg/mL with StartingBloc (registered trademark) (PBS) Blocking Buffer (manufactured by Thermo Fisher Scientific) to prepare a sample solution. On the other hand, a solution containing only ApoA1-free Blocking Buffer was prepared and used as a background solution. To the wells obtained in Example 1-1-1 was added 20 µL of the sample solution or 20 µL of the background solution, and the wells were allowed to stand at room temperature for 1 hour. By the above operation, the test substance was arranged on the substrate.

1-1-3. Preparation of Capturing Body 2

Anti ApoA1 Antibody P1A5 (manufactured by Sysmex Corporation) and magnetic beads (COOH FG beads, TAS8848N1140, diameter 180 nm, manufactured by TAMAGAWA SEIKI Co., Ltd.) were mixed with N-hydroxysuccinimide (KISHIDA CHEMICAL Co., Ltd., 010-38472) and 1-ethyl-3-(3-dimethylaminopropyl)carbodiimide hydrochloride (Dojindo Laboratories, W001), and beads were bound to the antibody. By this operation, a capturing body 2 having binding properties to the test substance (ApoA1) and containing a label (beads) was obtained.

1-1-4. Arrangement of Capturing Body 2 on Substrate

To the wells after the operation of Example 1-1-2 was added 40 µL of the capturing body 2 solution, and the wells were allowed to stand at room temperature for 1 hour. By this operation, the capturing body 2 was arranged on the substrate. After completion of the operation, the substrate containing the wells was set on the stage of a microscope (BZX710, manufactured by KEYENCE), the focus was set near the bottom of the well, and a bright field image (bright field image in the contact step 1) was acquired using a lens of ×40, NA=0.95.

1-2. Dissociation Step 1

The wells after the operation of Example 1-1-4 were sealed with a cover glass (manufactured by Matsunami Glass Ind., Ltd.). A magnet (N40, surface magnetic flux density 400 mT, manufactured by Niroku seisakusho Co., Ltd.) was approached to a height of 5 mm from the bottom of the well, whereby an external force for pulling the capturing body 2 (magnetic beads therein) upward was applied for 30 seconds. By this operation, the substance containing the capturing body 2 was dissociated from the substrate and released into a liquid. Meanwhile, the magnet was kept slightly swayed in the horizontal direction. Immediately after application of an external force, a bright field image (bright field image in the dissociation step 1) was acquired in the same manner as in Example 1-1-4.

1-3. Contact Step 2 and Dissociation Step 2

After the operation of Example 1-2, the magnet was separated to a position where the magnetic force did not completely reach the well, and was allowed to stand in that state for 5 minutes. By this operation, the capturing body 2 was again arranged on the substrate. After standing, a bright field image (bright field image in the contact step 2) was acquired in the same manner as in Example 1-1-4.

Thereafter, in the same manner as in Example 1-2, an external force was applied, and a bright field image (bright field image in the dissociation step 2) was acquired immediately thereafter.

1-4. Contact Step 3 and Dissociation Step 3

After the operation of Example 1-3, contact step 3 and dissociation step 3 were performed in the same manner as in Example 1-3, and each bright field image (bright field image in the contact step 3 and bright field image in the dissociation step 3) was acquired.

1-5. Contact Step 4 and Dissociation Step 4

After the operation of Example 1-4, contact step 4 and dissociation step 4 were performed in the same manner as in Example 1-3, and each bright field image (bright field image in the contact step 4 and bright field image in the dissociation step 4) was acquired.

1-6. Comparison 1 of Label-Derived Signal Arrangement Pattern on Substrate (Comparison Between Dissociation Steps)

Figure 11:
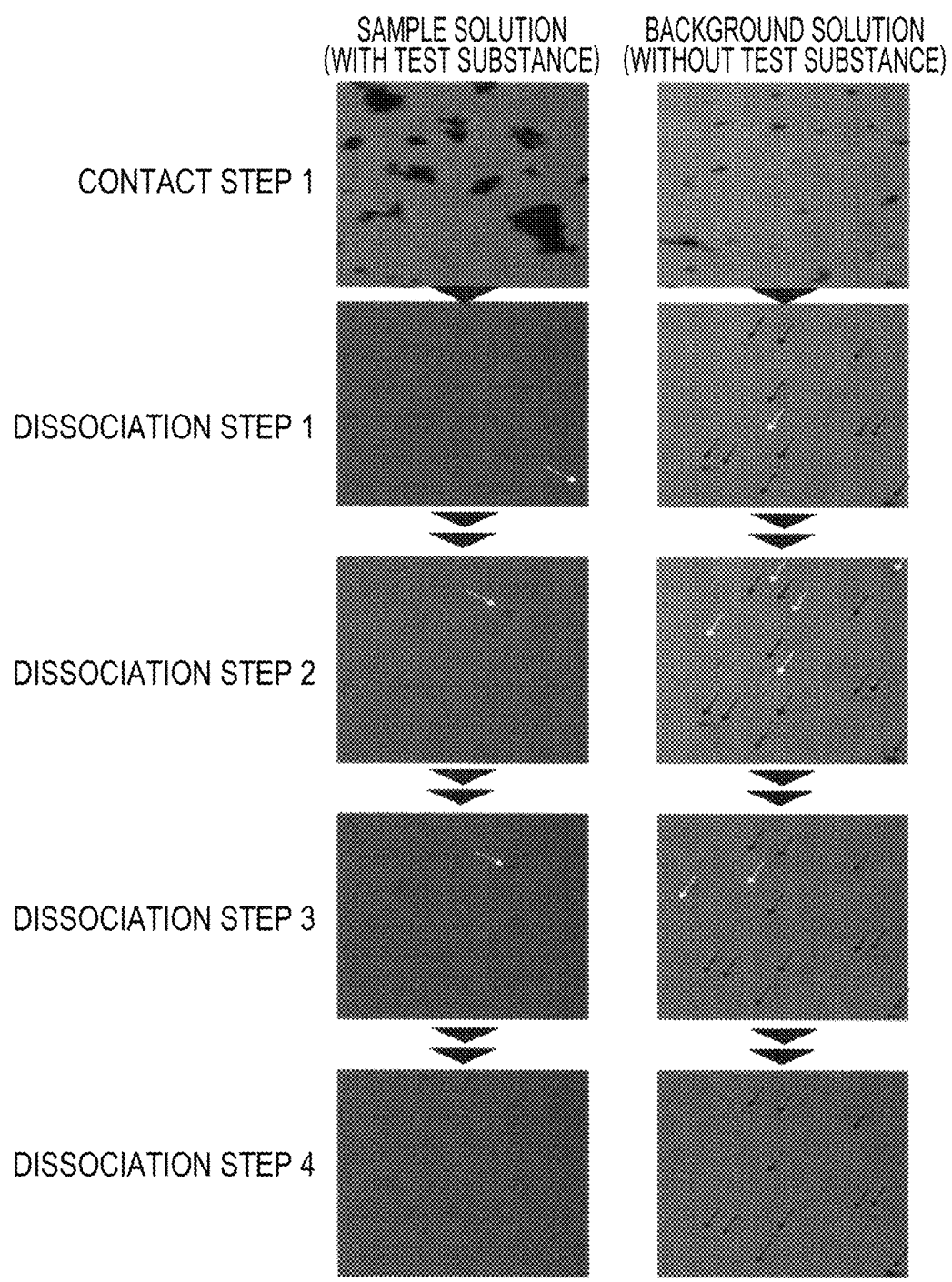
FIG. 11 shows bright field images of the result of Example 1 (a comparison result between dissociation steps). An arrow indicates a bright spot, a gray arrow indicates a bright spot with unchanged position even when comparing between any dissociation steps, and a white arrow indicates a bright spot whose position is changed between different dissociation steps.

The bright field image acquired in the above example is an image that can be discriminated as a bright spot signal by enlarging a label (magnetic beads). A part of the bright field image is shown in FIG. 11. In FIG. 11, an arrow indicates a bright spot, a gray arrow indicates a bright spot with unchanged position even when comparing between any dissociation steps, and a white arrow indicates a bright spot whose position is changed between different dissociation steps. The result of integrating the number of bright spots in a plurality of fields of view is shown in FIG. 12.

As shown in FIG. 11, it was found that the bright spots with unchanged position exist between any dissociation steps of the dissociation steps 1 to 4. It was suggested that these bright spots were signals derived from the capturing body 2 fixed on the substrate even after applying an external force, and were signals more specifically indicating a test substance. From this, a bright spot with unchanged position between contact steps was also said to be a signal derived from the capturing body 2 fixed on the substrate even after an external force was applied, and was suggested to be determined as a signal more specifically indicating a test substance.

As shown in FIG. 12, it was found that bright spots in the case of using a background solution (without a test substance), that is, signals based on nonspecific adsorption, were reduced by the dissociation step. In particular, after the dissociation step was performed twice (dissociation steps 2 to 4), nonspecific signal was 0.

Comparative Example 1 Detection of ApoA1 by Conventional Method

A test substance (ApoA1) was detected according to the ELISA method by B/F separation which has been conventionally normally performed. Specifically, it was performed as follows. The capturing body 2 was arranged on the substrate, in the same manner as in Example 1-1. Subsequently, the supernatant was removed, and 20 μL of PBS was added thereto. Thereafter, a bright field image was acquired with the focus set near the bottom of the well.

Figure 14:
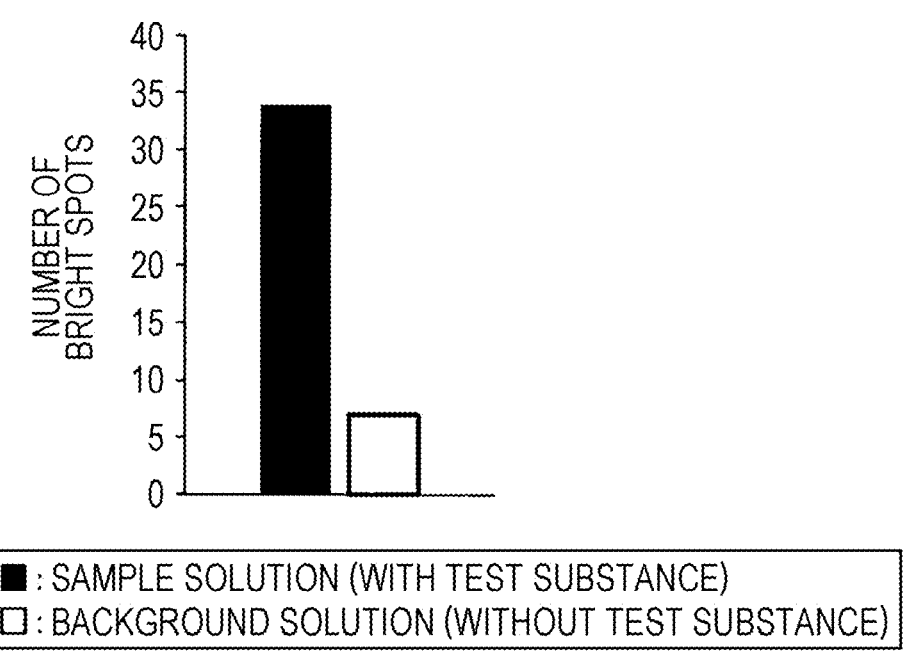
FIG. 14 is a graph of the number of bright spots, showing the result of Comparative Example 1. ■ indicates the case of using a sample solution (with a test substance), and □ indicates the case of using a background solution (without a test substance).

The bright-field image is shown in FIG. 13. The result of integrating the number of bright spots in a plurality of fields of view is shown in FIG. 14.

As shown in FIG. 13, according to the conventional method by B/F separation, even in the case of using a background solution (without a test substance), bright spots, that is, signals based on nonspecific adsorption remain to some extent.

What is claimed is:

1. A method for detecting a test substance, comprising a first contact step of bringing the test substance, a capturing body 1 that has binding properties to the test substance and is fixed to a substrate, and a capturing body 2 that has binding properties to the test substance and contains a label into contact with each other in a liquid to arrange at least a part of the capturing body 2 on the substrate;

after the first contact step, a first dissociation step of dissociating a part of substances containing the capturing body 2 from the substrate and releasing it into the liquid and an image P showing the label-derived signal arrangement pattern on the substrate is photographed; after the first dissociation step, a second contact step of bringing the test substance, the capturing body 1 that has binding properties to the test substance and is fixed to a substrate and the capturing body 2 that has binding properties to the test substance and contains a label into contact with each other in the liquid to arrange at least a part of the capturig body on the substrate;

after the second contact step, a second dissociation step of dissociating a part of substances containing the capturing body 2 from the substrate and releasing it into the liquid and an image Q showing the label-derived. signal arrangement pattern on the substrate is photographed; and comparing the label-derived signal arrangement pattern image P on the substrate after dissociation in the first dissociation step with the label-derived signal arrangement pattern image Q on the substrate after dissociation in the second dissociation step and detecting signals at substantially the same position as a signal indicating the test substance.

2. A method for detecting a test substance, comprising a first contact step of bringing the test substance, a capturing, body 1 that has binding, properties to the test substance and is fixed to a substrate, and a capturing body 2 that has binding properties to the test substance and contains a label into contact with each other in a liquid to arrange at least a part of the capturing body 2 on the substrate and an image X showing the label-derived signal arrangement pattern on the substrate is photographed;

after the first contact step, a first dissociation step of dissociating a part of substances containing the capturing body 2 from the substrate and releasing it into the liquid; after the first dissociation step, a second contact step of bringing the test substance, the capturing body 1 that has binding properties to the test substance and is fixed to a substrate, and the capturing body 2 that has binding properties to the test substance and contains a label into contact with each other in the liquid to arrange at least a part of the capturing body 2 on the substrate and an image Y showing the label-derived signal arrangement pattern on the substrate is photographed; and comparing the label-derived signal arrangement pattern image X on the substrate after contact in the first contact step with the label-derived signal arrangement pattern. image Y on the substrate after contact in the second contact step and detecting signals at substantially the same position as a signal indicating the test substance.

3. The method according to claim 1, wherein the capturing body 2 is dissociated from the substrate, by adjusting the strength of an external force applied to the capturing body 2 arranged on the substrate in the dissociation step.

4. The method according to claim 3, wherein the external force is an attractive force, and the capturing body 2 is dissociated from the substrate by applying an attractive force to the capturing body 2 arranged on the substrate in the dissociation step.

5. The method according to claim 4, wherein the contact step is in a state in which an attractive force weaker than the attractive force applied in the dissociation step is applied or a state in which no attractive force is applied.

6. The method according to claim 3, wherein the external force is an external force caused by at least one selected from the group consisting of magnetic force, Coulomb force, centrifugal force, fluid force, light, and sound wave.

7. The method according to claim 3, wherein the external force is an external force caused by at least one selected from the group consisting of magnetic force, Coulomb force, and sound wave.

8. The method according to claim 1, wherein the capturing body 2 comprises at least one member selected from the group consisting of antibodies, antigens, nucleic acids, receptors, ligands and aptamers that bind to the test substance, and carrier particles.

9. The method according to claim 8, wherein the carrier particles are at least one member selected from the group consisting of magnetic particles and charged particles.

10. The method according to claim 1, wherein the capturing body 1 comprises at least one member selected from the group consisting of antibodies, antigens, nucleic acids, receptors, ligands and aptamers that bind to the test substance.

11. The method according to claim 1, wherein a B/F separation step is not included between the first contact step and the first dissociation step.

12. The method according to claim 1, wherein a B/F separation step is not included between the second contact step and the second dissociation step.

13. The method according to claim 1, wherein
a moving image showing the label-derived signal arrangement pattern on the substrate in the first dissociation step and the second dissociation step are photographed, and
in the detection step, the label-derived signal that continues to be at substantially the same position from the first dissociation step to the second dissociation step in the moving image is detected as a signal indicating the test substance.

14. The method according to claim 2, wherein
a moving image showing the label-derived signal arrangement pattern on the substrate in the first contact step and the second contact step are photographed, and
in the detection step, the label-derived signal that continues to be at substantially the same position from the first contact step to the second contact step in the moving image is detected as a signal indicating the test substance.

15. A method for detecting a test substance, comprising
contacting the test substance with a capturing body 1 that has binding properties to the test substance and is fixed to a substrate and a capturing body 2 that has binding properties to the test substance and contains a label in a liquid to arrange at least a part of the capturing body 2 on the substrate;
after the contacting step, dissociating a part of substances containing the capturing body 2 from the substrate and releasing it into the liquid;
repeating more than once the steps of contacting and dissociating;
recording a label-derived signal arrangement pattern on the substrate after each dissociating,
comparing the label-derived signal arrangement patterns recorded in the recording step and detecting signals at substantially the same position in each label-derived signal arrangement pattern as a signal indicating the test substance.

16. The method according to claim 15, wherein the capturing body 2 is dissociated from the substrate, by adjusting the strength of an external force applied to the capturing body 2 arranged on the substrate in the dissociation step.

17. The method according to claim 16, wherein the external force is an attractive force, and the capturing body 2 is dissociated from the substrate by applying an attractive force to the capturing body 2 arranged on the substrate in the dissociation step.

18. The method according to claim 17, wherein the contact step is in a state in which an attractive force weaker than the attractive force applied in the dissociation step is applied or a state in which no attractive force is applied.

* * * * *